[54] ALKYLIDENE BISPHENOL PHOSPHITES AND PHOSPHATES HAVING 2,2,6,6-TETRAMETHYL PIPERIDINYL GROUPS AND SYNTHETIC RESIN COMPOSITION

[75] Inventors: Motonobu Minagawa, Koshigaya; Yutaka Nakahara, Iwatsuki; Toshihiro Shibata, Omiya; Ryozo Arata, Kyoto, all of Japan

[73] Assignee: Adeka Argus Chemical Co., Ltd., Urawa, Japan

[21] Appl. No.: 687,090

[22] Filed: Dec. 28, 1984

[30] Foreign Application Priority Data

Dec. 29, 1983 [JP] Japan .................... 58-249828

[51] Int. Cl.$^4$ .............................................. C08K 5/34
[52] U.S. Cl. ........................................ 524/99; 546/19; 546/209; 546/221; 546/222; 558/78; 558/79; 558/85; 558/86; 524/325; 524/333; 524/336; 524/338; 524/341; 524/342; 524/344
[58] Field of Search ................. 260/927 R, 260/937; 936, 937; 524/99; 546/19, 209, 221, 222; 558/78, 79, 85, 86

[56] References Cited

U.S. PATENT DOCUMENTS 4,259,492  3/1981  Rasberger ........................... 546/21

Primary Examiner—John Kight
Assistant Examiner—Kriellion Morgan

[57] ABSTRACT

Alkylidene bisphenol phosphites and phosphates having 2,2,6,6-tetramethyl piperidinyl groups are provided having the formula:

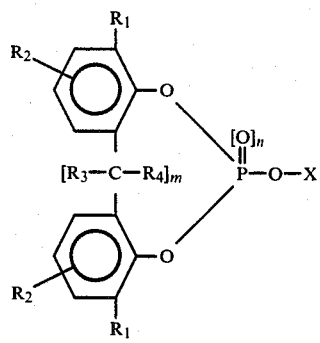

wherein:
$R_1$ is alkyl having from one to about twelve carbon atoms;
$R_2$, $R_3$ and $R_4$ are each selected from the group consisting of hydrogen and alkyl having from one to about twelve carbon atoms;
m is 0 or 1;
n is 0 or 1;

X is selected from the group consisting of

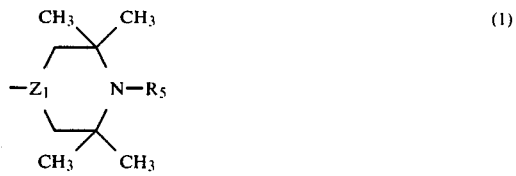

wherein:
$R_5$ is selected from the group consisting of hydrogen, oxyl $O^2$, alkyl having from one to about twelve carbon atoms; arylalkyl having from seven to about eighteen carbon atoms; 2,3-epoxypropyl, acyl having from one to about eight carbon atoms and

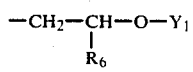

in which $R_6$ is selected from the group consisting of hydrogen, alkyl having from one to about twelve carbon atoms and phenyl, and $Y_1$ is selected from the group consisting of hydrogen; acyl having from one to about twelve carbon atoms; and

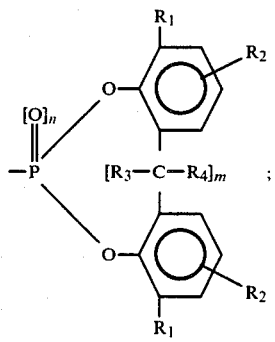

$Z_1$ is selected from the group consisting of

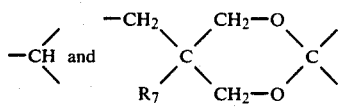

wherein $R_7$ is alkyl from one to about twelve carbon atoms;
and

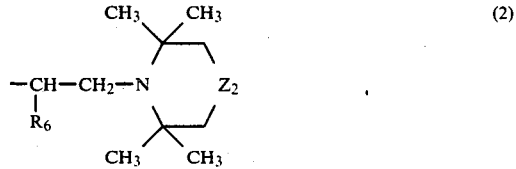

wherein:

(Abstract continued on page 2.)

$R_6$ is selected from the group consisting of hydrogen, alkyl having from one to about twelve carbon atoms and phenyl; and $Z_2$ is selected from the group consisting of

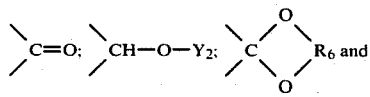 and

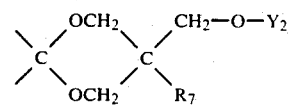

in which $R_7$ is alkyl having from one to about twelve carbon atoms;

$R_6$ is alkylene having from one to about eight carbon atoms and $Y_2$ is selected from the group consisting of hydrogen and acyl having from one to about eight carbon atoms.

36 Claims, No Drawings

ALKYLIDENE BISPHENOL PHOSPHITES AND PHOSPHATES HAVING 2,2,6,6-TETRAMETHYL PIPERIDINYL GROUPS AND SYNTHETIC RESIN COMPOSITION

Synthetic resins such as polyethene, polypropylene, polystyrene and polyvinyl chloride show a strong tendency to deteriorate in physical properties at elevated temperatures and when exposed to ultraviolet light. The deterioration is evidenced by, among other things, a decrease in viscosity, a tendency to become brittle, and discoloration. This deterioration can be accompanied by distortion, cracking, and powdering of the material. To overcome these difficulties, many stabilizers have been proposed for combination with synthetic resins.

No single stabilizer has proved adequate, and combinations of stabilizers are consequently used almost exclusively. Most stabilized synthetic resins on the market contain one or more of such stabilizer combinations. The deterioration appears to be due to a combination of factors, and a combination of stabilizers is therefore more capable of coping with the various types of deterioration. However, the retention of good physical properties over long periods of time remains rather difficult to achieve.

Of the many stabilizer systems that have been proposed for polyolefins, one particularly satisfactory stabilizer system is described in U.S. Pat. No. 3,255,136, patented June 7, 1966 to Arthur Hecker, Otto S. Kauder and Norman Perry. This stabilizer system comprises three stabilizers: an organic mono- or polyhydric phenol, an organic phosphite, and a thiodipropionic acid ester. An additional fourth ingredient, which is preferred but not essential, is a polyvalent metal salt of an organic acid. These three and four stabilizers together give an enhanced stabilization which is not obtainable from any of them alone, or in combinations of two.

In these combinations, the phenol alone gives an improved resistance to embrittlement and reduction in melt viscosity of polypropylene at elevated temperatures, but little assistance as to maintenance of color. The phosphite alone is a rather poor stabilizer in preventing deterioration in the first two properties, but it does assist in resisting discoloration. The two together are worse than the phenol alone in every respect except color, which is intermediate.

The thiodipropionic acid ester by itself only improves resistance to embrittlement. The polyvalent metal salt of an organic acid by itself only prevents discoloration. In combinations with the phenol, the color is worse than with the salt alone, and combinations with phosphite only, discoloration is prevented. The effectiveness of all three or four ingredients taken together against all of these types of deterioration is therefore particularly surprising.

The organic phosphite can be any organic phosphite having the formula $(RA)_3-P$, in which A can be oxygen or sulfur or a mixture of the same, and R is aryl, alkyl, cycloalkyl, aralkyl or aralkaryl in any combination. A variety of tris-alkaryl phosphites are disclosed, such as tris-(tertiary-octyl-phenyl)phosphite and tris-(tertiary-nonyl-phenyl)phosphite, but no tris-(alkaryl)-phosphites having more than one alkyl group per phenyl group.

Organic phosphites have been widely used as stabilizers for polyolefins and similar polymeric materials, particularly polyvinyl chloride, and many different types of phosphites, some of rather complex structure, have been proposed. U.S. Pat. Nos. 3,255,136 and 3,655,832 have suggested organic phosphite-phenol transesterification products, the preferred phenol being a bisphenol. Other types of tris-(alkaryl)phosphites esters have been disclosed in U.S. Pat. Nos. 2,220,113; 2,220,845; 2,246,059; 2,419,354; 2,612,488; 2,732,365; 2,733,226; and 2,877,259. Additional tris-(alkaryl)-phosphites are disclosed in U.S. Pat. No. 3,167,526 to Nicholson, patented Jan. 26, 1965; U.S. Pat. No. 3,061,583 to Huhn and Sheets, patented Oct. 30, 1962; U.S. Pat. No. 3,829,396 to Oakes and Cross, patented Aug. 13, 1974; French Pat. Nos. 1,496,563 to U.S. Rubber Company, délivré Aug. 21, 1967, and 1,497,390 to Ethyl Corporation, délivré Aug. 28, 1967; and British Pat. Nos. 1,058,977 published Feb. 15, 1967, to Hooker Chemical Corporation and 1,143,375, published Feb. 19, 1969, to Uniroyal Inc.

Oakes et al disclose bis-(2,4-di-tertiary-butyl-phenol)-cyclohexyl phosphite and 2,4-di-(tertiary butyl)phenyl dicyclohexyl phosphite, which are liquids.

French Pat. No. 1,496,563 described phosphites derived from 2,6-di-tertiary-butyl-hydroquinone and 2,5-di-tertiary-butyl-hydroquinone, and it is suggested that they can be used with thiodipropionic acid esters of olefin polymers.

British Pat. No. 1,143,375 has a similar disclosure; tris-(2,5-di-tertiary-butyl-4-hydroxy-phenyl)phosphite is disclosed.

British Pat. No. 1,058,977 discloses 2,4,6-tri-substituted aryl phosphites, the substituents including tertiary-butyl groups.

French Pat. No. 1,497,390 discloses tris-(3,5-di-alkyl-4-hydroxy-phenyl)phosphites, as well as tris-(3-isopropyl-5-tertiary-butyl-phenyl)phosphite.

Kuriyama et al U.S. Pat. No. 3,558,554 patented Jan. 26, 1971, provides olefin polymer compositions containing as a stabilizer an organophosphite having the general formula:

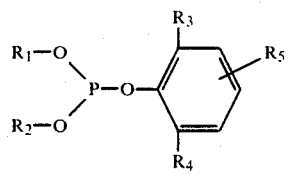

wherein
  $R_1$ and $R_2$ each represents a member selected from the group consisting of substituted and unsubstituted alkyl, cycloalkyl, aryl, alkaryl, aralkyl, and aliphatic thio ether groups and $R_3$, $R_4$ and $R_5$ each represents a member selected from the group consisting of hydrogen and alkyl, cycloalkyl, aryl, alkaryl, and aralkyl groups, at least one of said $R_3$ and $R_4$ being a tertiary butyl group.

Suitable organo phosphites include, for example, di-n-butyl (2-t-butyl-cresyl)phosphite, di-n-hexyl(2-t-butyl-m-cresyl)phosphite, di-n-hexyl(2-t-butyl-p-cresyl)phosphite, di-n-octyl(2-t-butyl-p-cresyl)phosphite, di-n-butyl-3,4-di-t-butyl-phenyl)phosphite, di-n-butyl-(2,6-di-t-butyl-p-cresyl)phosphite, di-phenyl(2-t-butyl-p-cresyl)phosphite, tri-(2-t-butyl-p-cresyl)-phosphite, di(ethylthioethyl)-(2-t-butyl-p-cresyl)-phosphite, di(octylthioethyl)(2-t-butyl-p-cresyl)phosphite, and tri(2,4-di-t-butyl-phenyl)phosphite.

Many organic phosphites have been proposed as stabilizers for polyvinyl chloride resins, and are employed either alone or in conjunction with other stabilizing compounds, such as polyvalent metal salts of fatty acids and alkyl phenols. Such phosphite stabilizers normally contain alkyl or aryl radicals in sufficient number to satisfy the three valences of the phosphite, and typical phosphites are described in the patent literature, for example, W. Leistner et al., U.S. Pat. Nos. 2,564,646 of Aug. 14, 1951, 2,716,092 of Aug. 23, 1955, and 2,997,454 of Aug. 2, 1961.

Organic phosphites have also been added as stabilizers in amounts of 0.01 to 1%, preferably 0.05% to 0.2% by weight, to high molecular weight polycarbonate plastics, for example the polycarbonate of 2,2'-bis(4-hydroxyphenyl)propane of molecular weight 10,000 and up to over 50,000 as disclosed by G. Fritz in U.S. Pat. No. 3,305,520 of Feb. 21, 1967.

A. Hecker in U.S. Pat. No. 2,860,115 of Nov. 11, 1958 discloses compositions of organic phosphites with metal salts of carboxylic acids used in olefin polymers.

Phosphites are also employed in conjunction with other stbilizers such as a polyhydric phenol in the stabilization of polypropylene and other synthetic resins against degradation upon heating or ageing under atmospheric conditions. The polyhydric phenol is thought to function as an antioxidant in such combinations. Disclosures by R. Werkheiser, U.S. Pat. Nos. 2,726,226 of Dec. 6, 1975; I. Salyer et al, 2,985,617 of May 23, 1961; L. Friedman, 3,039,993 of June 19, 1962; W. Nudenberg, 3,080,338 of Mar. 5, 1963; C. Fuchsman, 3,082,187 of Mar. 19, 1963; H. Orloff et al, 3,115,465 of Dec. 24, 1963; A. Nicholson, 3,167,526 of Jan. 26, 1965; A. Hecker et al, 3,149,093 of Sept. 15, 1964, 3,244,650 of Apr. 5, 1966 and 3,225,136 and 3,255,151 of June 7, 1966; C. Bawn, 3,352,820 of Nov. 14, 1967; D. Miller, 3,535,277 of Oct. 20, 1970; J. Casey, 3,568,657 of June 22, 1971; C. Abramoff 3,856,728 of Dec. 24, 1974; M. Minagawa, 3,869,423 of Mar. 4, 1975 and 3,907,517 of Sept. 23, 1975; and British Pat. Nos. 846,684, 851,670, and 866,883 are representative of stabilizer combinations including organic phosphites, polyhydric phenols, and other active ingredients.

The importance of organic phosphites as stabilizers for synthetic resins has led to the development of a large variety of special phosphites intended to provide improved stabilizing effectiveness and compatability and ease of compounding with the resin and with other stabilizers commonly used. However, the phosphites which have been proposed have not been entirely successful, partly because of their complicated structure, which makes them costly to prepare, and partly because of their difficulty of preparation.

Among these special phosphites, L. Friedman, U.S. Pat. No. 3,047,608 of July 31, 1962 discloses a class of bisphosphites having the formula:

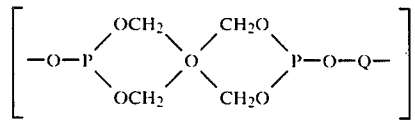

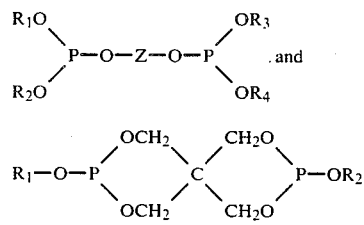

in which $R_1$, $R_2$, $R_3$ and $R_4$ are alkyl or aryl and Z is $-CH_2CH_2SCH_2CH_2O-$, $-C_2CH_2SO_2C_2H_2-(-CH_2CH_2O-)_x$ or $-(CHCH_3CH_2)_x$ where x is at least two, and in U.S. Pat. No. 3,053,878 of Sept. 11, 1962 a class of linear phosphite polymers from the formula:

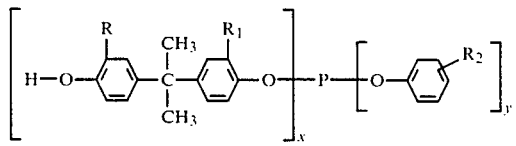

in which

Q is the alkylene or arylene portion of a dihydric alcohol or dihydric phenol.

R. Morris et al in U.S. Pat. No. 3,112,286 of Nov. 26, 1963 discloses phosphites having the formula:

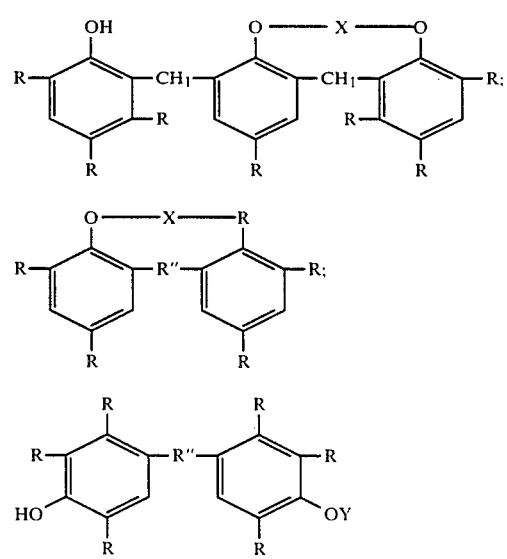

in which

R represents a bulky hydrocarbon group such as t-butyl, t-amyl, t-hexyl, cyclohexyl, t-pentyl, t-octyl, phenyl and the like;

$R_1$ represents hydrogen and R;

$R_3$ represents an alkyl group from six to twenty carbon atoms which is preferably in the meta or para position;

x represents a number of from 1 to 3 inclusive;

y represents a number of from 0 to 2 inclusive and the sum of the numerical value of x+y is always exactly 3.

D. Brown, U.S. Pat. No. 3,297,631 of Jan. 10, 1967 discloses condensation products of phosphorus compounds with bisphenols and trisphenols which may be represented by the structures:

where:

X is selected from the following: >P—OR'; >P—R';

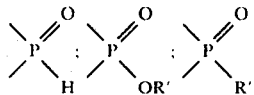

and Y is selected from the following: —P(OR')₂;

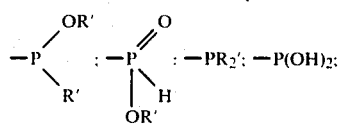

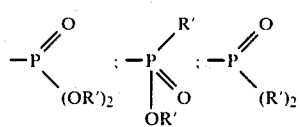

R is hydrogen, alkyl of one to sixteen carbon atoms or aryl or a combination of these; R' is alkyl of one to sixteen carbon atoms or aryl, and R" is alkylidene of one to sixteen carbon atoms or an aryl-substituted alkylidene.

C. Baranauckas, U.S. Pat. No. 3,305,608 of Feb. 21, 1967, discloses phenolic phosphites useful as polymer stabilizers prepared by reacting a triorganophosphite, a polyol, and an aromatic material having two to six phenolic hydroxyl groups at 60° to 180° C. in specified proportions.

C. Brindell, U.S. Pat. No. 3,412,064 of Nov. 19, 1968 discloses phenolic phosphites represented by the general formula:

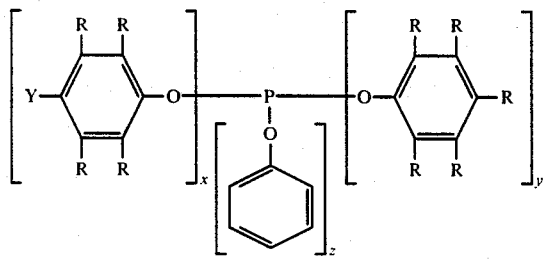

where x is from 1 to 3, y and z each from 0 to 2, x+y+z=3, R is hydrogen or alkyl and Y is hydroxyl or a group of the formula:

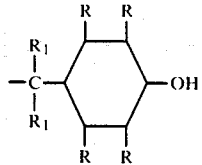

where R is hydrogen or alkyl.

M. Larrison, U.S. Pat. No. 3,419,524 of Dec. 31, 1968, discloses phosphites useful as polymer stabilizers having the formula:

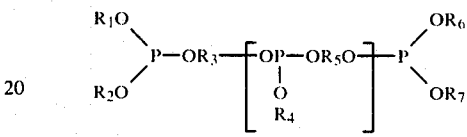

where $R_1$, $R_2$, $R_4$, $R_6$ and $R_7$ are aryl or haloaryl, and $R_3$ and $R_5$ are a polyalkylidene glycol or an alkylidene bisphenol or a hydrogenated alkylidene bisphenol or a ring-halogenated alkylidene bisphenol from which the two terminal hydrogens have been removed.

O. Kauder et al, U.S. Pat. No. 3,476,699 of Nov. 4, 1969 and U.S. Pat. No. 3,655,832 of Apr. 11, 1972 discloses organic phosphites containing a free phenolic hydroxyl group and defined by the formula:

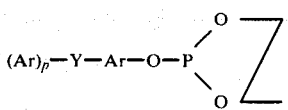

wherein Z is selected from the group consisting of hydrogen and aliphatic, cycloaliphatic, aromatic, heterocyclic and (Ar)$_p$—Y—Ar groups, taken in sufficient number to satisfy the valences of the two phosphite oxygen atoms; Y is a polyvalent linking group selected from the group consisting of oxygen; aliphatic, cycloaliphatic and aromatic hydrocarbon groups attached to each Ar group through a carbon atom not a member of an aromatic ring; oxyaliphatic; thioaliphatic, oxycycloaliphatic, thiocycloaliphatic; heterocyclic, oxyheterocyclic, thioheterocyclic, carbonyl, sulfinyl; and sulfonyl groups; Ar is a phenolic nucleus which can be phenyl or a polycarbocyclic group having condensed or separate phenyl rings; each Ar group is either connected through an oxygen atom to a phosphite group or contains a free phenolic hydroxyl group, or both; and p is a number, one or greater, and preferably from one to four, which defines the number of Ar groups linked to Y.

L. Friedman, U.S. Pat. No. 3,516,963 of June 23, 1970 discloses phosphites having the formula:

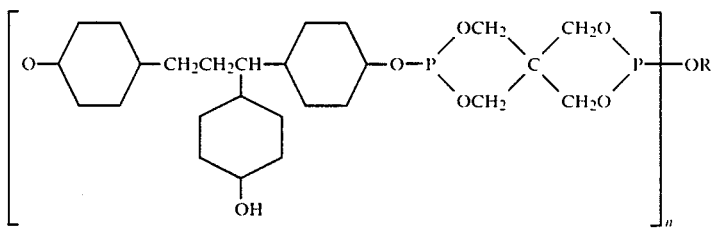

where R is alkyl, alkenyl, aryl, aralkyl, haloaryl, haloalkyl or

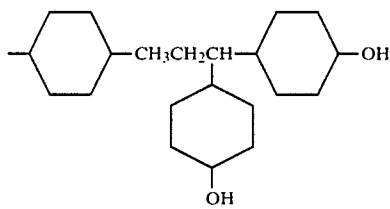

and n is an integer of at least 1. n can be 2, 3, 4, 5, 6, 7, 8, 10, 50, 100 or even more.

D. Brown et al in U.S. Pat. Nos. 3,510,507 of May 5, 1970 and 3,691,132 of Sept. 12, 1972 discloses polyolefins stabilized with polyphosphites, polyphosphates, polyphosphonites, polyphosphonates, polyborates, polycarbonates, and polysilanes which are condensation products of a 4,4'-bisphenol with a condensing or linking agent which may be of the ester type, such as the esters of triaryl or mixed aryl-alkyl compounds, or the acid halide type. Brown's condensation product stablizers have molecular weights between 600 and 8000 or higher and are described by the structural formula:

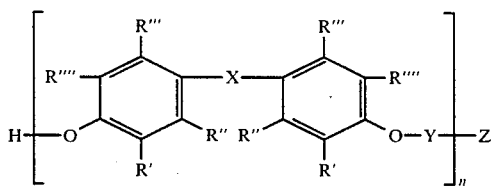

where X is selected from the group consisting of

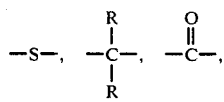

—C—C, and C—A—C— where A is a $C_1$ to $C_{16}$ alkylene or an arylene; R', R", R'", and R"" are selected from the group consisting of hydrogen, $C_1$ to $C_{18}$ alkyls, and an aryl group; Y is selected from the group of

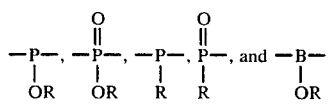

where R is hydrogen, a $C_1$ to $C_{18}$ alkyl or aryl;

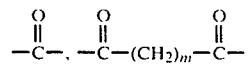

where m is 0 to 10, preferably 4 to 8,

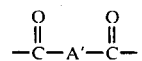

where A' is $(CH_2)_n$—S—$(CH_2)_n$ or —$(CH_2)_n$—S—$(CH_2)_m$—S—$(CH_2)_n$ where n is 0 to 10, preferably 2 and m is 0 to 10, preferaby 5;

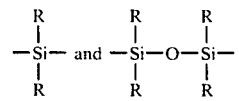

where R is an alkyl, preferably methyl, and Z is

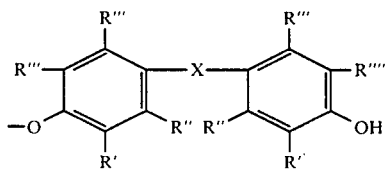

where R', R", R'", R"", and X correspond respectively to the R', R", R'", R"", and X previously selected when n has a value from 1 to 15, or may be derived from the compound used to introduce Y into the product when n has a value from 2 to 15, for example, —R or —OR where R is hydrogen, an alky, or aryl. When Y in the formula of Bown's stabilizer is

the stabilizer is a type of hydroxyaryl phosphite. Similarly, when Y in the formula is

the stabilizer is a hydroxyaryl carbonate.

Bown's condensation products are described as especially effective in high molecular weight solid polyolefins when used together with a dialkyl sulfide costabilizer such as dilauryl thiodipropionate, distearyl thiodipropionate, ditridecyl thiodipropionate, dicetyl sulfide, bis(tetradecylmercapto)paraxylylene, and 10, 24-dithiotetracontane.

J. Floyd et al in German published application No. 2505071 of Aug. 14, 1975 abstracted in *Chemical Abstracts* 1976. Volume 84, abstract No. 5945f, discloses low molecular weight polycarbonate esters of bisphenols such as 2,2-bis(3-t-butyl-4-hydroxyphenylpropane) and 4,4'-butylidene bis(6-t-butyl-3-methylphenol) prepared in such a way as to contain few or no free phenolic hydroxyl groups as being highly effective heat and light stabilizers for polyolefins and giving a synergistic effect with distearyl thiodipropionate, tris(nonylphenyl)phosphite, and distearyl pentaerythritol diphosphite.

U.S. Pat. No. 4,252,750 to Buysch et al, patented Feb. 24, 1981, provides phosphorous acid esters corresponding to the general formula

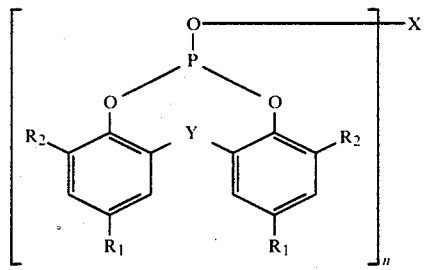

wherein
$R_2$ is a benzyl, α-methylbenzyl, α,α-dimethylbenzyl, cyclopentyl or cyclohexyl radical;
$R_1$ is a $C_1$–$C_9$ alkyl, a $C_5$–$C_6$ cycloalkyl, a $C_7$–$C_9$ aralkyl or a $C_6$–$C_{10}$ aryl radical;
Y is a sulphur atom or a group HC—$R_3$, in which $R_3$ is a hydrogen atom a $C_1$–$C_6$ alkyl, a cyclohexyl or cyclohexenyl radical;
X is a hydrogen atom, an optionally substituted single-bond to four-bond straight-chain or branched-chain $C_1$–$C_{18}$ aliphatic radical, A $C_7$–$C_{18}$ aralkyl radical or a $C_6$–$C_{18}$ aromatic radical, each of which radicals may optionally contain olefinic double bonds and/or hetero atoms, preferably N, O and/or S atoms, and
n is an integer from 1 to 4, preferably from 1 to 2, provided that when X is a hydrogen atom the n is 1.

U.S. Pat. No. 4,288,391, to Spivack, patented Sept. 8, 1981, provides alkylated 1,1'-biphenyl-2,2'-diylphosphites represented by the formula

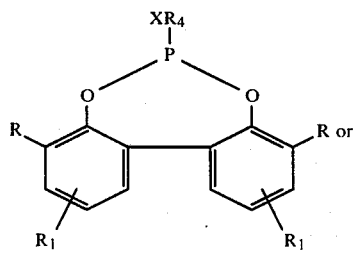

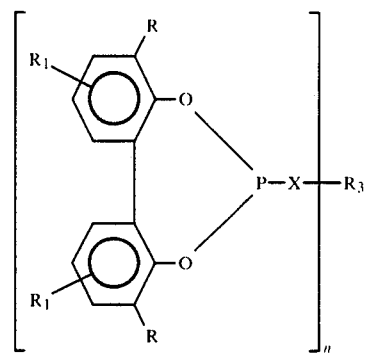

wherein
R is an alkyl group of 1 to 18 carbon atoms,
$R_1$ is hydrogen or an alkyl group of 1 to 18 carbon atoms, and
$R_2$ is an alkyl group of 1 to 20 carbon atoms, phenyl, phenyl substituted by 1 to 3 alkyl groups each having 1 to 8 carbon atoms or by two alkyl groups each having 1 to 8 carbon atoms and by —COOR$_4$ where $R_4$ is alkyl of 1 to 18 carbon atoms,
$R_3$ is an n-valent radical selected from the group consisting of a straight- or branched-chain alkylene of 2 to 12 carbon atoms, a straight- or branched-chain alkane-triyl, -tetrayl, -pentayl or -hexayl of 3 to 6 carbon atoms, alkenylene of 4 to 6 carbon atoms, cycloalkylene of 6 to 12 carbon atoms, 1,4-cyclohexanedimethylene, arylene or arenetriyl of 6 to 10 carbon atoms, p-xylylene, phenylene—E—phenylene where E is a direct bond, —O—, —S—, —NR$_5$—, where $R_5$ is alkyl of 1 to 18 carbon atoms; a straight- or branched-chain alkylene or alkylidene of 1 to 12 carbon atoms or cycloalkylidene of 5 to 6 carbon atoms, said arylene or said phenylene—E—phenylene substituted by 1 to 4 alkyl groups each having 1 to 8 carbon atoms, —(CH$_2$)$_x$S(CH$_2$)$_x$— where x is 2 to 6, dipentaerythrityl, and

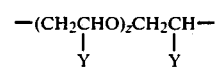

where Y is hydrogen, methyl or ethyl and z is 1 to 10,
X is oxygen or sulfur, and
n is 2 to 6.

U.S. Pat. No. 4,318,845 to Spivack et al, patented Mar. 9, 1982, provides alkanolamine esters of 1,1'-biphenyl-2,2'-diyl-and alkylidene-1,1'-biphenyl-2,2'-diyl-cyclic phosphites corresponding to the formula:

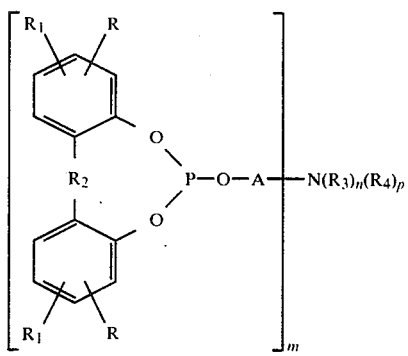

such that when m=1, n=1 and p=1, m=2, n=1 and p=0, m=3, n and p are zero, and wherein
R is an alkyl group of 1 to 18 carbon atoms,
$R_1$ is hydrogen or an alkyl group of 1 to 18 carbon atoms;
$R_2$ is a direct bond or lower alkylene of 1 to 12 carbon atoms;
A is alkylene of 1 to 6 carbon atoms or cycloalkylene of 5 to 6 carbon atoms;
$R_3$ is an alkyl of 1 to 18 carbon atoms, or

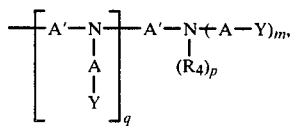

wherein
Y is

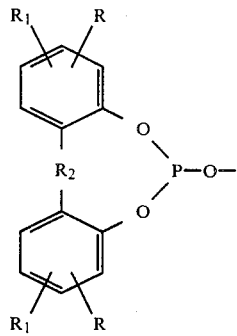

A' is alkylene of 1 to 6 carbon atoms or cycloalkylene of 5 to 6 carbon atoms,
m' is 1 or 2,
p is 0 or 1, and
q is 0–5
with A, R, $R_1$, $R_2$ being as previously defined; provided that when p and q are 0, —N—A'—N can be a diazacyloalkyl group of 2 to 10 carbon atoms or, when m is 1 and p is 0, N—$R_3$ is an azacycloalkyl group of 2 to 10 carbon atoms or an azaoxacycloalkyl group of 3 to 7 carbon atoms; and
$R_4$ is alkyl of 1 to 18 carbon atoms.

U.S. Pat. No. 4,362,830 to Minagawa et al, patented Dec. 7, 1982, provides hindered bis-phenol phenyl phosphites having the structure:

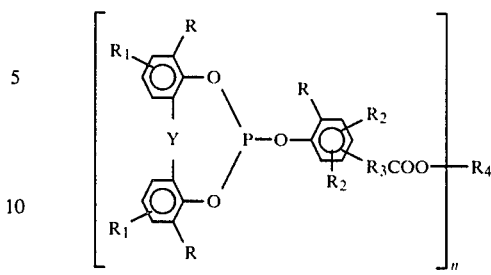

wherein:
R is selected from the group consisting of alkyl having from one up to about eighteen carbon atoms; cycloalkyl having from three up to about twelve carbon atoms; alkaryl and aryl having from six to about eighteen carbon atoms; preferably, a bulky group such as iso, secondary or tertiary alkyl having from three to about ten carbon atoms; or cycloalkyl having six to twelve carbon atoms;
$R_1$ and $R_2$ are each selected from the group consisting of hydrogen; alkyl having from one to about eighteen carbon atoms; cycloalkyl having from three up to about twelve carbon atoms; alkaryl and aryl having from six to about eighteen carbon atoms; and are preferably in a position ortho to a phenolic hydroxyl or phenoxy group, if available;
$R_3$ is alkylene having from one to about six carbon atoms;
$R_4$ is selected from the group consisting of alkylene, cycloalkylene, and aralkylene, the residue of a monohydric or polyhydric alcohol, having from one to about eighteen carbon atoms, and from none to three hydroxyl groups (originally one to four hydroxyl groups);
Y is selected from the group consisting of a direct carbon to carbon bond; thio sulfur —S—; oxy oxygen —O—; alkylidene having from one to about six carbon atoms; and cycloalkylidene having from four to about eight carbon atoms; and
n is 1, 2, 3, or 4, according to the valence of $R_4$.

U.S. Pat. No. 4,371,646 to Minagawa et al, patented Feb. 1, 1983, provides 2,6-di-tertiary butyl phenyl phosphites having the structure

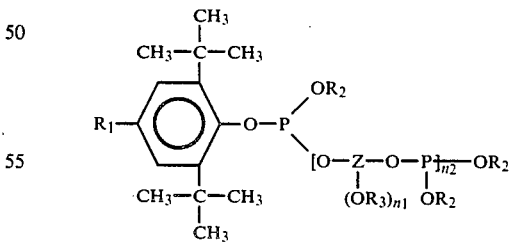

wherein:
$R_1$ is selected from the group consisting of hydrogen, methyl, ethyl, and $(CH_2)_m COOR$, where R is selected from the group consisting of alkyl having from one up to about ten carbon atoms; cyclaolkyl having from three up to about twelve carbon atoms; alkaryl and aryl having from six to about twelve carbon atoms; and m is a number within the range from 0 to 5;

$R_2$ is selected from the group consisting of hydrogen, alkyl having from one to about twenty-two carbon atoms; cycloalkyl having from three up to about twelve carbon atoms; alkaryl and aryl having from six to about eighteen carbon atoms; the residue of a polyhydric alcohol having from two to about eighteen carbon atoms, and from two to three hydroxyl groups; and the residue of a polyphenol having from six to about eighteen carbon atoms and from two to about ten phenolic hydroxyl groups;

$R_3$ is selected from the group consisting of hydrogen and $P(OR_2)_2$;

Z is the bivalent to tetravalent residue of a polyhydric alcohol having from two to about eighteen carbon atoms, and from two to five hydroxyl groups; or of a polyphenol having from six to about eighteen carbon atoms and from two to about ten phenolic hydroxyl groups;

$n_1$ is 0 or 1; and $n_2$ is a number from 1 to 5.

U.S. Pat. No. 4,371,647 to Minagawa et al, patented Feb. 1, 1983, provides 2,6-di-tertiary butyl phenyl pentaerythritol spiro bis-phosphites having the structure:

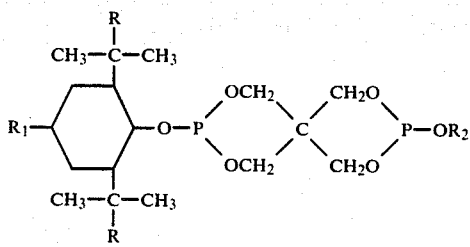

wherein:

R is alkyl having from one to six carbon atoms;

$R_1$ is methyl or ethyl;

$R_2$ is selected from the group consisting of alkyl having from one up to about eighteen carbon atoms; cycloalkyl having from three up to about twelve carbon atoms; and alkaryl and aryl having from six to about thirty carbon atoms; such groups substituted with from one to about four oxy ether —O— and/or carboxylic ester —COO— groups ; the residue of a polyhydric alcohol having from two to about eighteen carbon atoms, and from two to about ten hydroxyl groups; and the residue of a polyphenol having from six to about eighteen carbon atoms and from two to about ten phenolic hydroxyl groups.

In accordance with the present invention, alkylidene bisphenol phosphites and phosphates having 2,2,6,6-tetramethyl piperidinyl groups are provided having the formula:

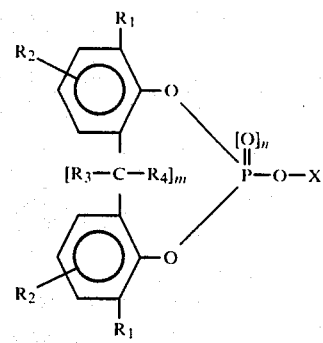

wherein:

$R_1$ is alkyl having from one to about twelve carbon atoms;

$R_2$, $R_3$ $R_4$ are each selected from the group consisting of hydrogen and alkyl having from one to about twelve carbon atoms;

m is 0 or 1;

n is 0 or 1;

X is selected from the group consisting of

wherein:

$R_5$ is selected from the group consisting of hydrogen, oxyl O, alkyl having from one to about twelve carbon atoms; aryl alkyl having from seven to about eighteen carbon atoms; 2,3-epoxypropyl, acyl having from one to about eight carbon atoms and

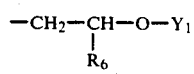

in which $R_6$ is selected from the group consisting of hydrogen, alkyl having from one to about twelve carbon atoms and phenyl, and $Y_1$ is selected from the group consisting of hydrogen; acyl having from one to about twelve carbon atoms; and

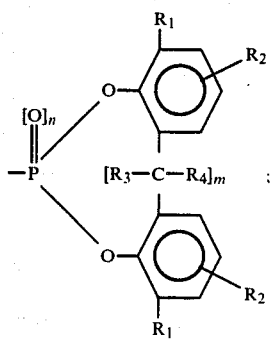

$Z_1$ is selected from the group consisting of $$-\overset{\diagup}{\underset{\diagdown}{CH}} \text{ and } -\overset{\diagup}{\underset{R_7}{C}}\begin{matrix}-CH_2\\ \\ -CH_2-O\end{matrix}\overset{CH_2-O}{\underset{}{C}}\diagdown$$

wherein R₇ is alkyl having from one to about twelve carbon atoms; and $$-\underset{R_6}{CH}-CH_2-N\begin{matrix}CH_3 & CH_3\\ \diagdown C\diagup\\ \diagup \quad \diagdown\\ CH_3 & CH_3\end{matrix}Z_2 \quad (2)$$

wherein:

R₆ is selected from the group consisting of hydrogen, alkyl having from one to about twelve carbon atoms and phenyl; and Z₂ is selected from the group consisting of $$\diagdown C=O; \quad \diagdown CH-O-Y_2; \quad \diagdown C\overset{O}{\underset{O}{\diagup\diagdown}}R_6 \text{ and}$$

$$\diagdown\underset{OCH_2}{\overset{OCH_2}{C}}\diagup\overset{CH_2-O-Y_2}{\underset{R_7}{C}}\diagdown$$

in which R₇ is alkyl having from one to about twelve carbon atoms; R₆ is alkylene having from one to about eight carbon atoms and Y₂ is selected from the group consisting of hydrogen and acyl having from one to about eight carbon atoms.

It will be seen that according to the selection of X, Z₁ and Z₂ the following subgenera fall within formula I:

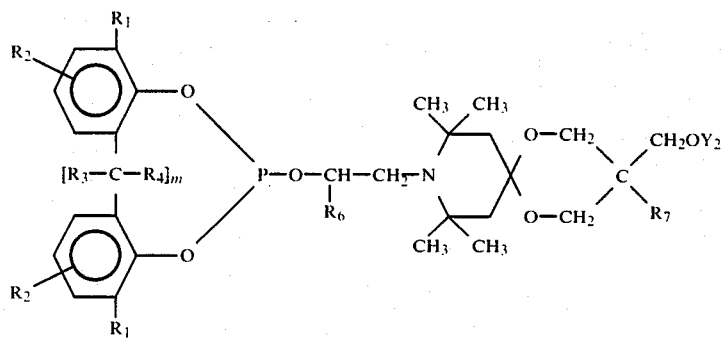

VII

Exemplary $R_1$, $R_2$, $R_3$, $R_4$, $R_5$, $R_6$ and $R_7$ alkyl include methyl, ethyl, propyl, isopropyl, n-butyl, isobutyl, sec-butyl, tert-butyl, amyl, isoamyl, tert-amyl, hexyl, isohexyl, tert-hexyl, heptyl, isoheptyl, isooctyl, octyl, 2-ethylhexyl, tert-octyl, nonyl, isononyl, sec-nonyl, tert-nonyl, decyl, isodecyl, tert-decyl, undecyl, isoundecyl, and dodecyl;

Exemplary $R_5$ arylalkyl include benzyl, phenylethyl, phenylpropyl, phenylbutyl, phenylamyl, phenylhexyl, phenyloctyl, phenylnonyl, and phenyldodecyl;

Exemplary $R_6$ alkylene include ethylene, 1,2-propylene, 1,3-propylene, 2,2-dimethyl-1,3-propylene, 1,2-butylene and 1,2-ocytylene;

Exemplary $R_5$, $Y_1$ and $Y_2$ acyl include formyl, acetyl, propionyl, butyroyl, valeryl, hexanoyl, heptanoyl, octanoyl, acryloyl, methacryloyl and benzoyl.

Typical compounds falling within the invention as represented by the formula (I) are:

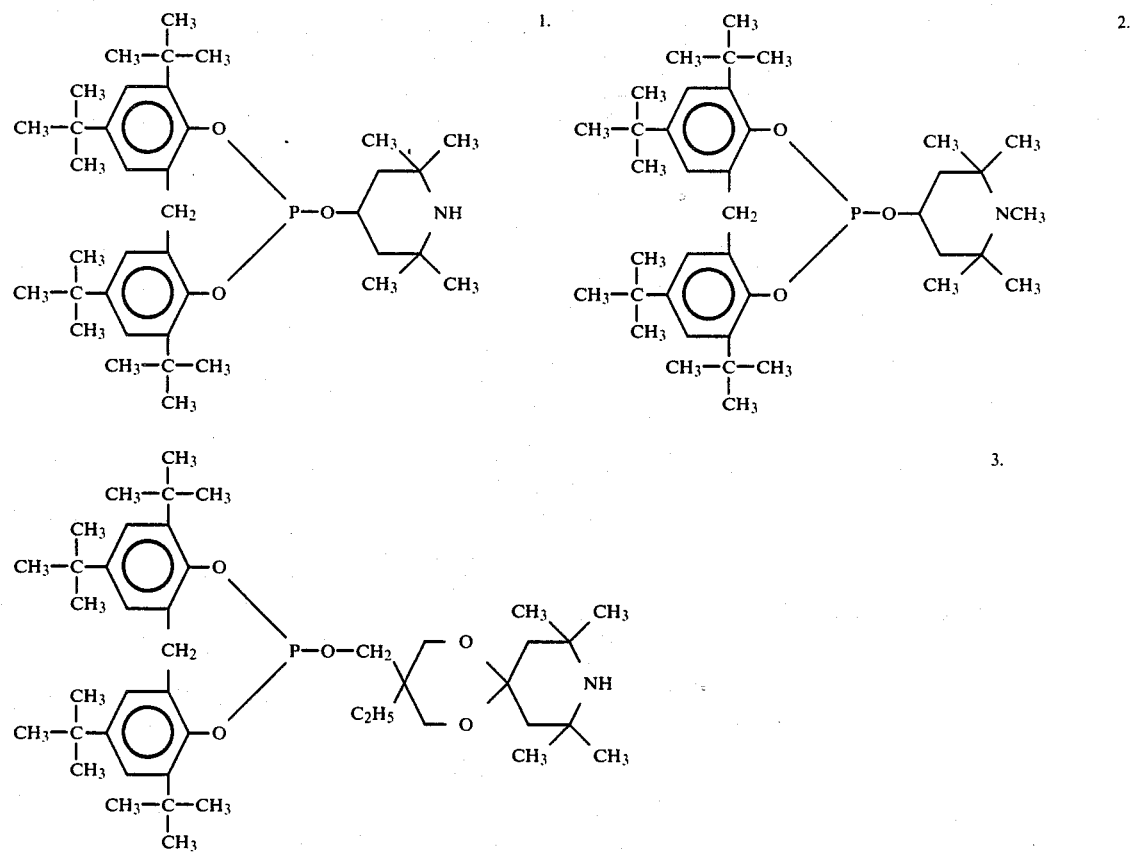

-continued
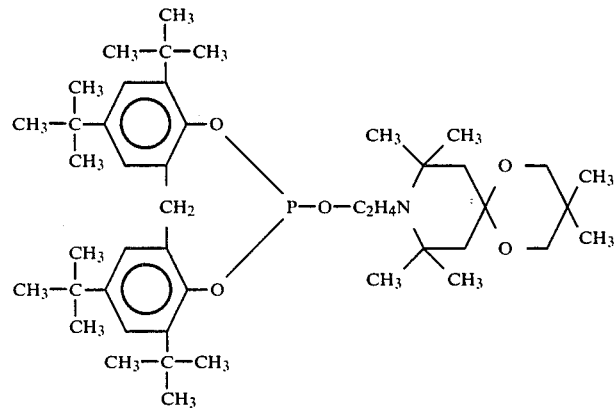
4.
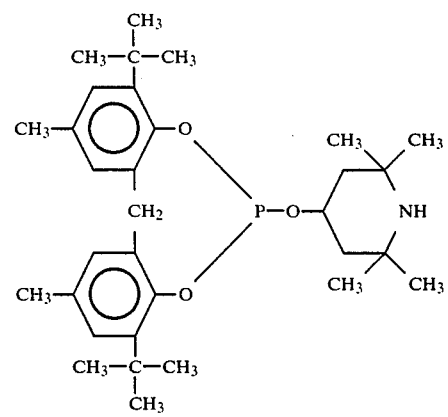
5.
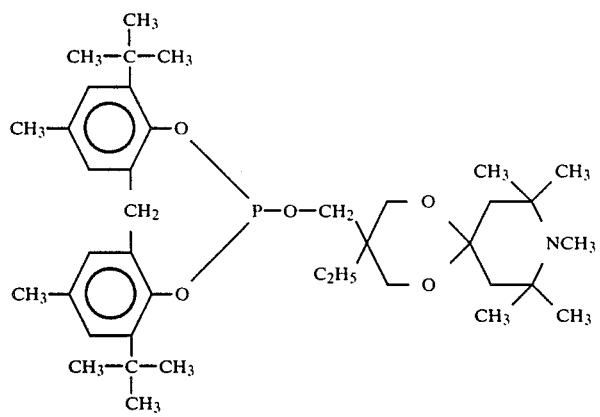
6.
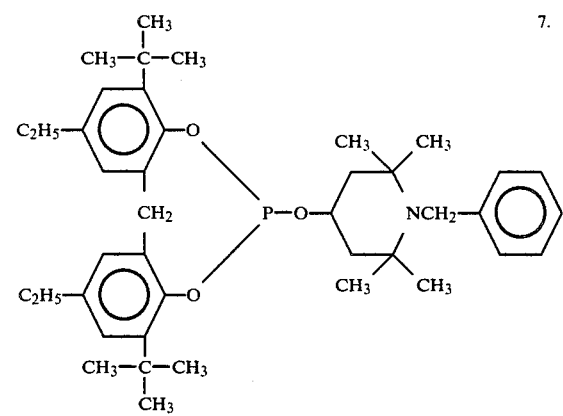
7.
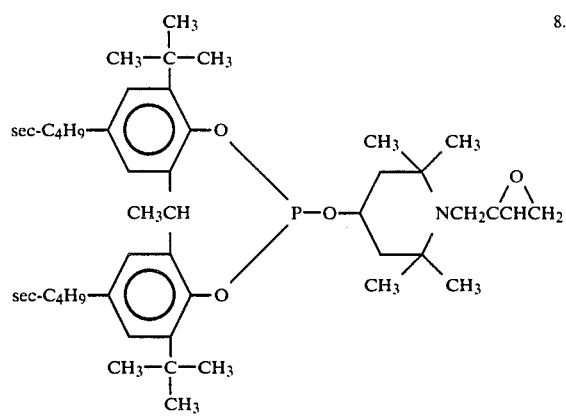
8.
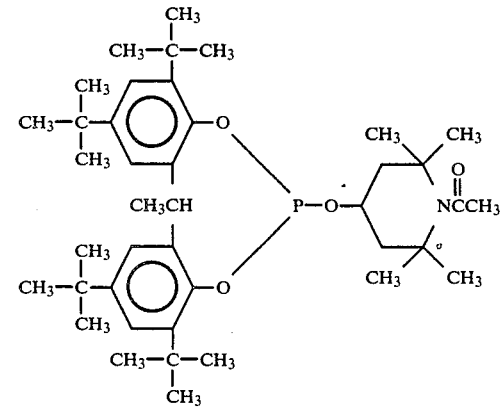
9.
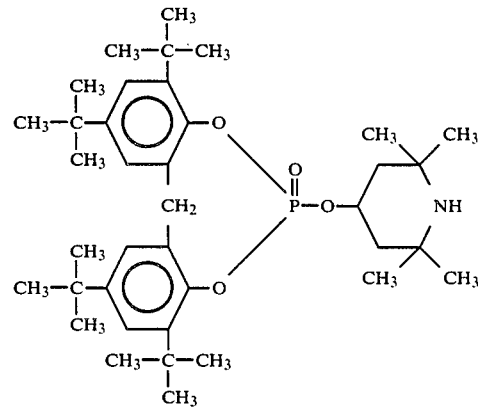
10.

11.
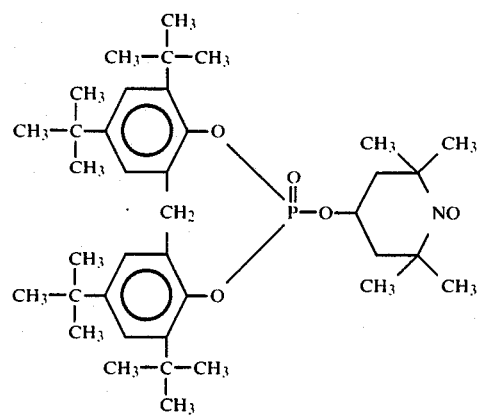
12.
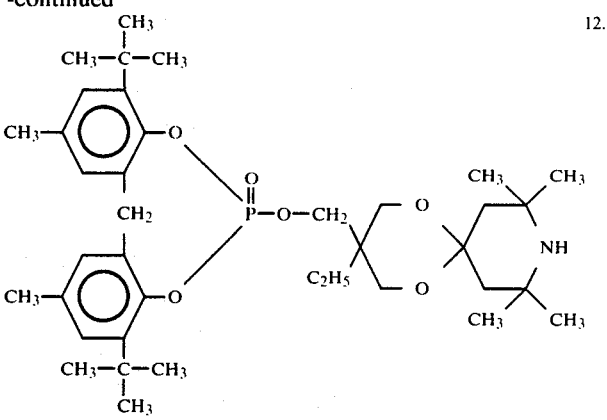
13.
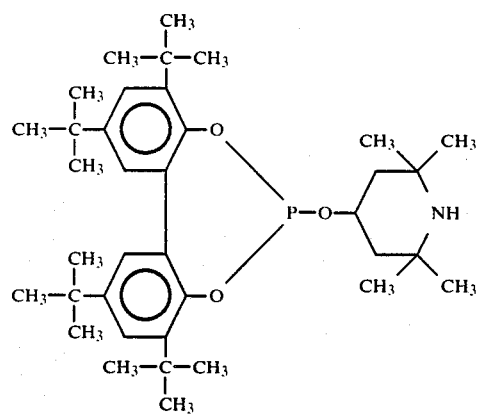
14.
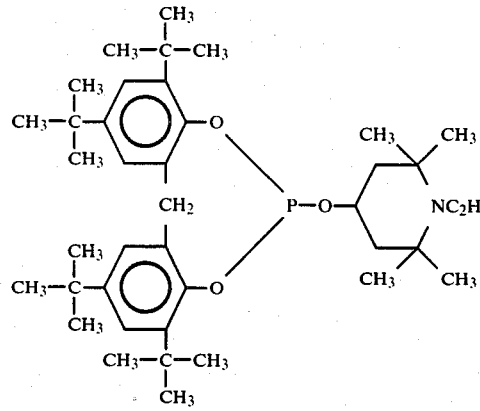 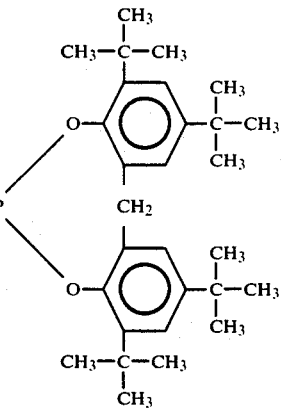
15.
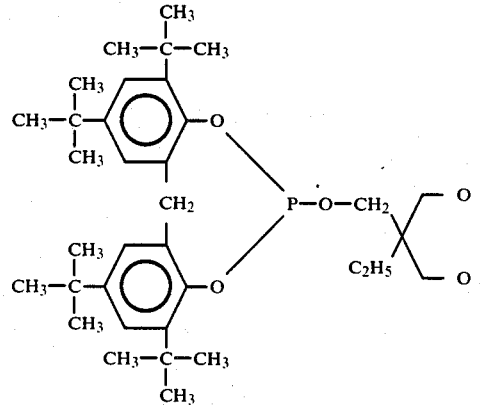 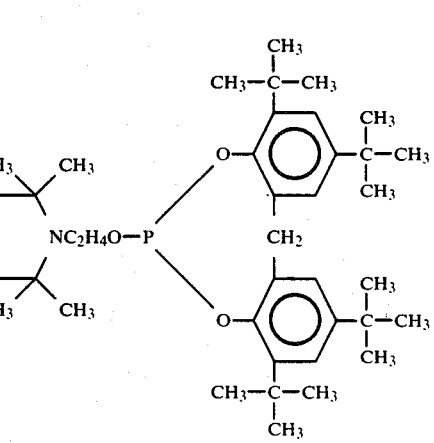

-continued
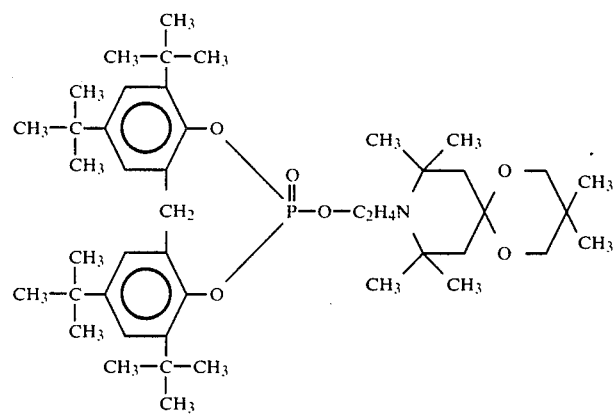 16.
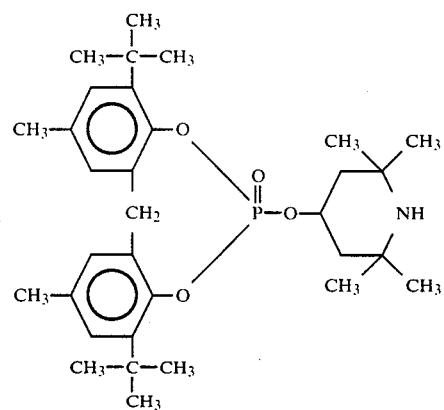 17.
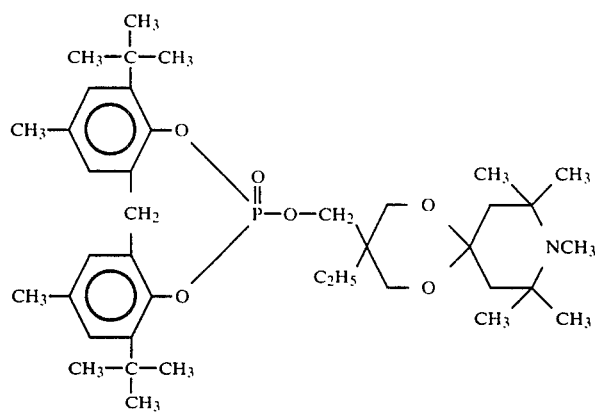 18.
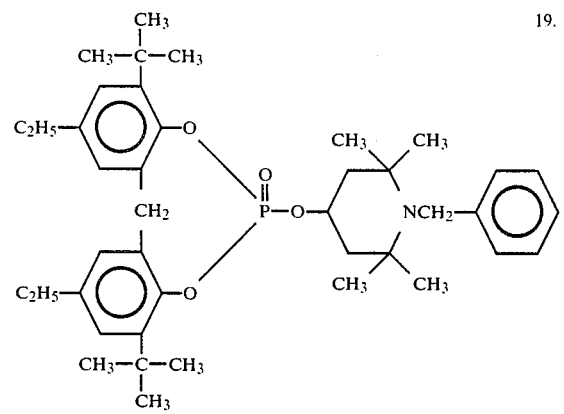 19.
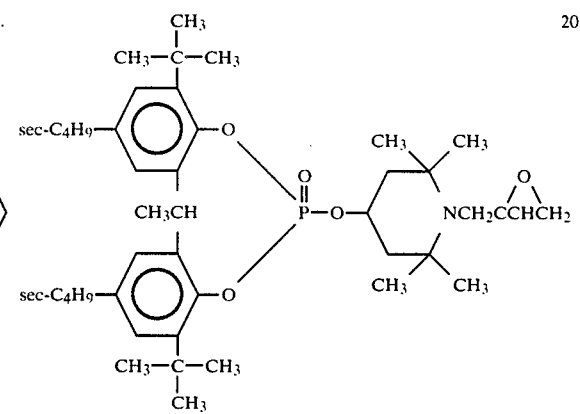 20.
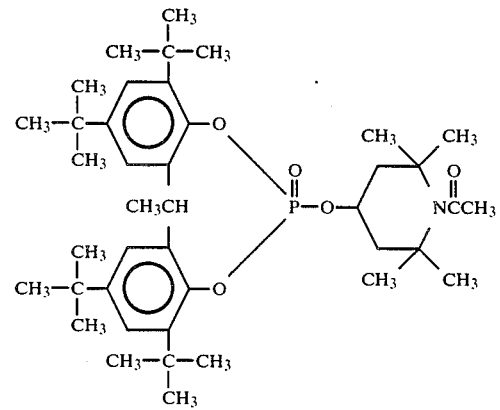 21.
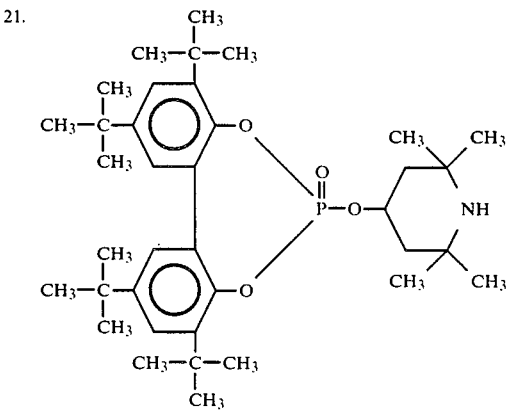 22.

-continued
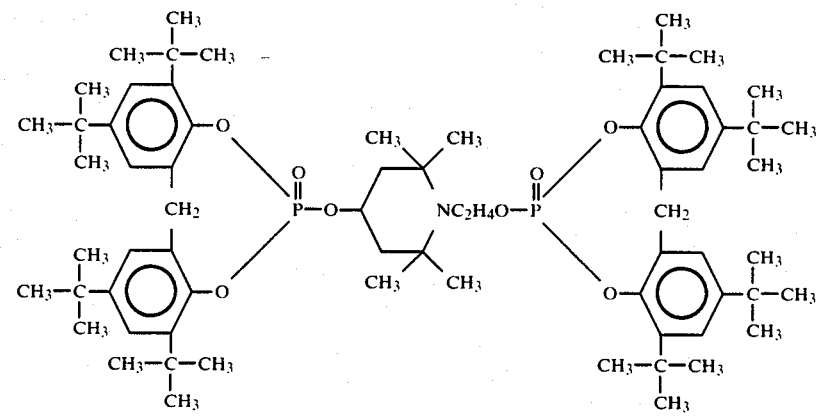
23.
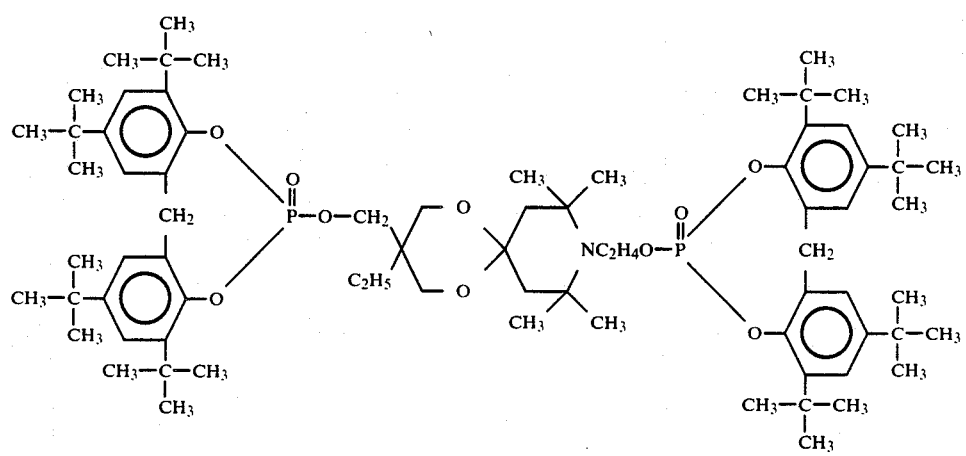
24.
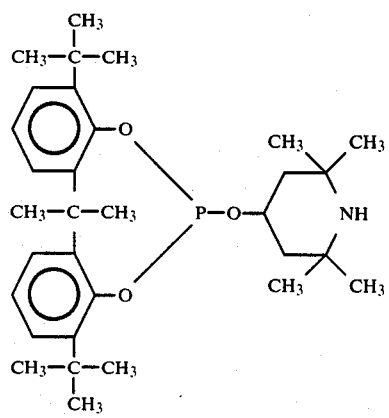
25.
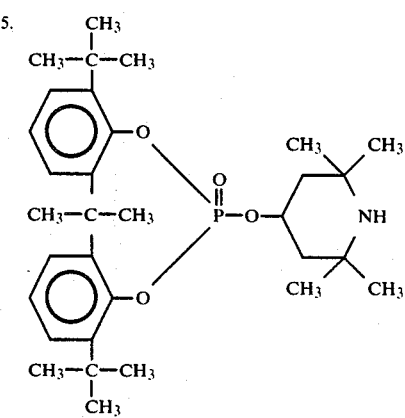
26.

-continued
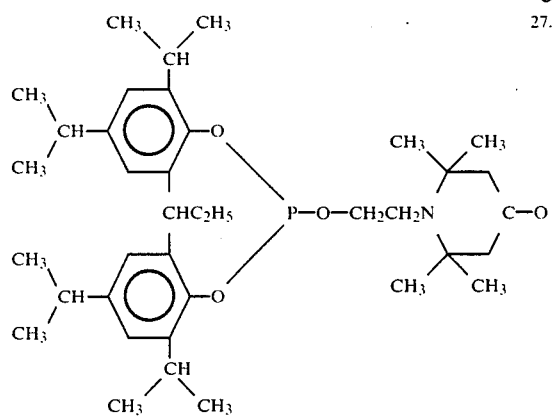
27.
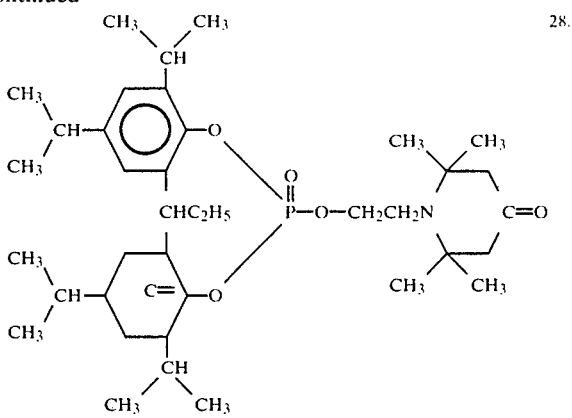
28.
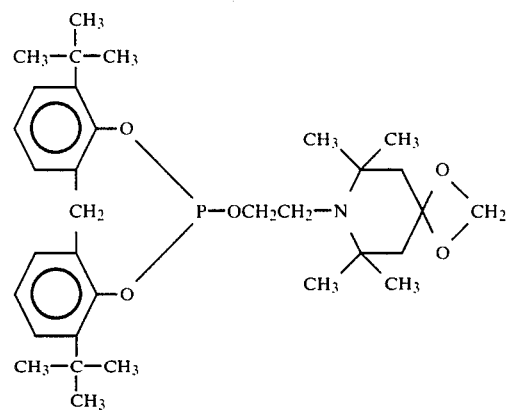
29.
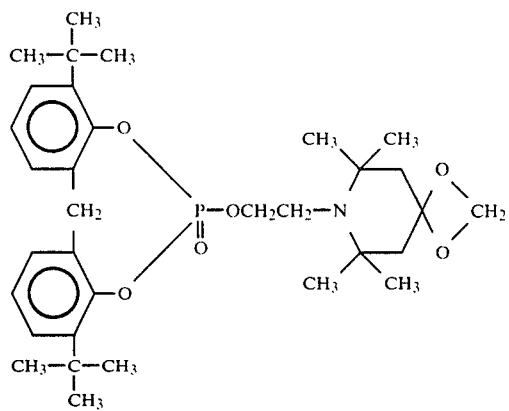
30.
These compounds can be readily prepared by reacting the corresponding bisphenol chlorophosphite or chlorophosphate of the formula
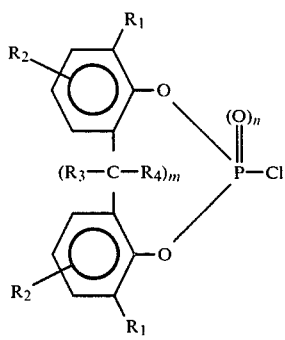
with the piperidyl compound X—OH.
The following Examples are illustrative:
EXAMPLE I
Preparation of
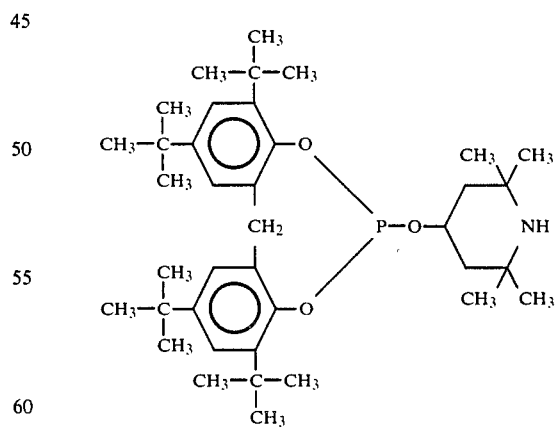
from the bisphenol chlorophosphite of the formula:

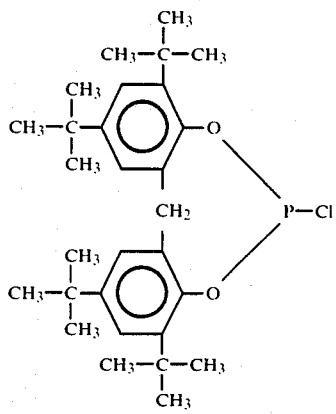

The bisphenol chlorophosphite, 2.5 g, 2,2,6,6-tetramethyl-4-piperidinol 1.6 g, triethylamine 0.5 g and dichloroethane 25 ml were heated and stirred at 80° to 84° C. for ten hours under a stream of nitrogen gas. The precipitated triethylamine hydrochloride was filtered off, and then the solvent was stripped off. Benzene 50 ml was added, and the mixture washed with water and dried. The benzene was distilled off, and 2.5 g of white solid was obtained, M.P.=108°-113° C., I.R.: 840 cm$^{-1}$ (based on P—O—phenyl), 1010 cm$^{-1}$ : (based on P—O—alkyl).

EXAMPLE II

Preparation of

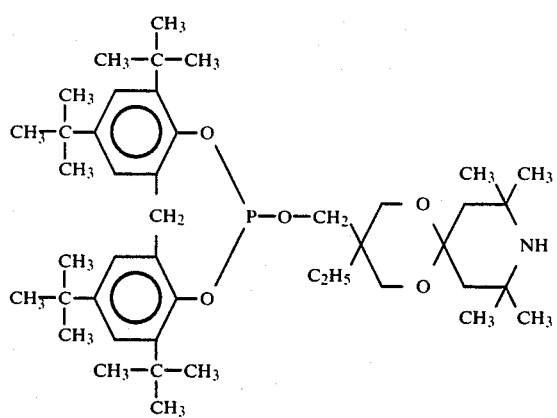

The bisphenol chlorophosphite of Example I, 2.5 g, 9-aza-8,8,10,10-tetramethyl-3-ethyl-3-hydroxymethyl-1,5-dioxaspiro (5.5) undecane, 2.8 g triethylamine 0.5 g and dichloroethane 25 ml were heated and stirred at 80° 1 to 84° C. for ten hours under a stream of nitrogen gas. The precipitated triethylamine hydrochloride was filtered off, and then the solvent was stripped off. Benzene 50 ml was added, and the mixture washed with water and dried. The benzene was distilled off, and 2.8 g of product, M.P. 102°-104.5° C. was obtained. I.R.: 830 cm$^{-1}$ (based on P—O—phenyl), 1020 cm$^{-1}$ (based on P—O—alkyl), 1100 cm$^{-1}$(based on C—O—C).

EXAMPLE III

Preparation of

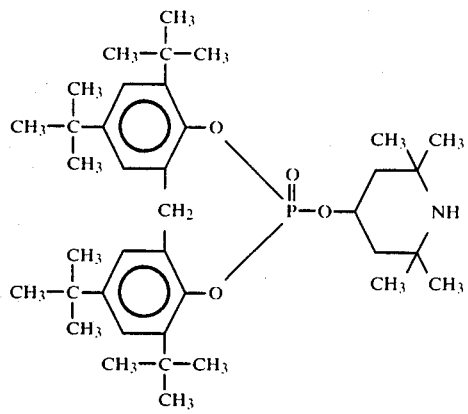

from bisphenol chlorophosphate of the formula:

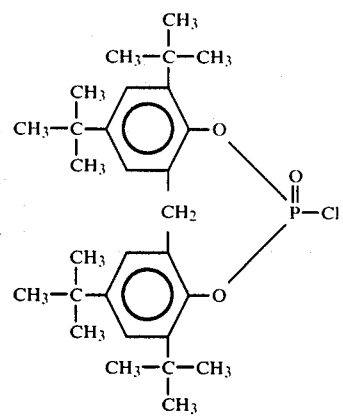

The bisphenol chlorophosphate, 3.0 g, 2,2,6,6-tetramethyl-4-piperidinol 1.8 g, triethylamine 0.6 g and dichloroethane 25 ml were heated and stirred at 80° to 84° C. for 15 hours under a stream of nitrogen gas. The precipitated triethylamine hydrochloride was filtered off, and then the solvent was stripped off. Benzene 50 ml was added, and the mixture washed with water and dried. The benzene was distilled off, and a glassy solid product, M.P. 93°-97° C., was obtained. I.R.: 945 cm$^{1}$ (based on P—O—phenyl), 1020 cm$^{1}$ (based on P—O—alkyl).

Small amounts of the stabilizer of this invention when combined with synthetic resin improve the heat stability of the resin. The amount of the stablizer is generally within the range from about 0.001 to about 5 parts by weight, preferably from about 0.01 to about 3 parts by weight, per 100 parts by weight of resin.

Synthetic resins that can have their resistance to deterioration enhanced with the polymeric-stablizer compound according to this invention include α-olefin polymers such as polyethylene, polypropylene, polybutene, poly-3-methylbutene, or mixtures thereof and with copolymers other monomers such as ethylene-vinyl acetate copolymer; ethylene-propylene copolymer; polystyrene; polyvinyl acetate; polyacrylic esters; copolymers from styrene and another monomer (for example, maleic anhydride, butadine, and acrylonitrile); acrylonitrile-butadienestyrene copolymer, acrylic acid ester-butadiene-styrene copolymer, methacrylic acid ester-butadine-styrene copolymer, polymethacrylate esters such as polymethacrylate, polyvinyl alcohol; polyvinyl formal; polyvinyl butyral; linear polyesters, polyamides; polycarbonates; polyacetals; polyurethanes; cellulosic resins; phenol-formaldehyde resins; urea-formaldehyde resins; melamine-formaldehyde resins; epoxy resins; unsaturated polyester resins; silicone resins; halogen-containing resins such as polyvinyl chloride, polyvinylidene chloride, polyvinylidene fluoride, and copolymers thereof, and rubbers such as isoprene rubber, butadiene rubber, epichlorohydrin rubber, chloroprene rubber, and blends of any of the above.

The alkylidene bisphenol phosphite and phosphate stabilizers of the invention can be combined with conventional heat stablizers such as phenolic antioxidants, polyvalent metal salts of organic acids, organic phosphites, thioethers, and other known heat stabilizers, thereby constituting heat and light stabilizer compositions of the invention.

The phenolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

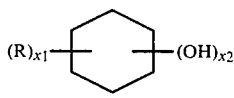

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl.
$x_1$ and $x_2$ are integers from one to four, and the sum of $x_1$ and $x_2$ does not exceed six.

The polycyclic phenol phenol is one having at least two aromatic nuclei linked by a polyvalent linking radical, as defined by the formula:

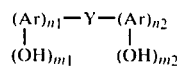

wherein
Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy

R' is aryl, alkyl or cycloalkyl, or thiohydrocarbon groups having from one to about thirty carbon atoms, and carboxyl

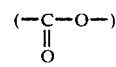

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydyric polycyclic phenol has the structure:

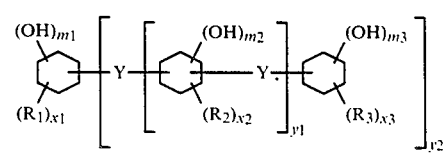

wherein
$R_1$, $R_2$ and $R_3$ are inert substituent groups as described in the previous paragraph;
$m_1$ and $m_3$ are integers from one to a maximum of five;
$m_2$ is an integer from one to a maximum of four;

x₁ and x₃ are integers from zero to four, and
x₂ is an integer from zero to three;
y₁ is an integer from zero to about six and
y₂ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa- and thia-substituted such groups; tetrahydrofuranes, esters and triazine groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least one carbon in a chain or cyclic arrangement connect the aromatic groups, such as:

—CH₂—CH₂—; —(CH₂)₅—; —CH₂—;

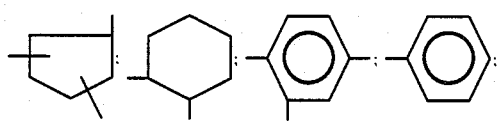

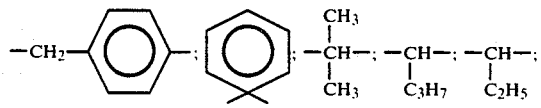

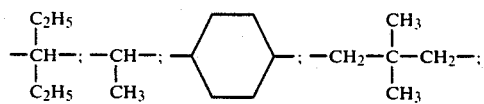

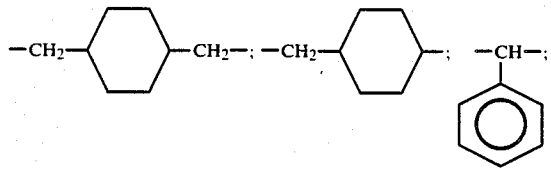

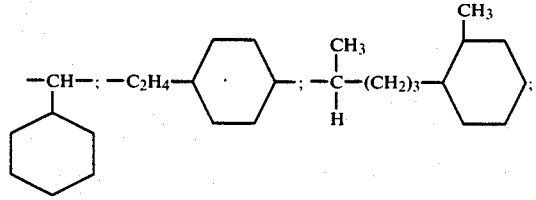

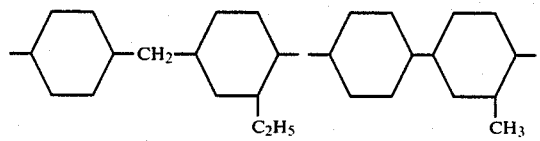

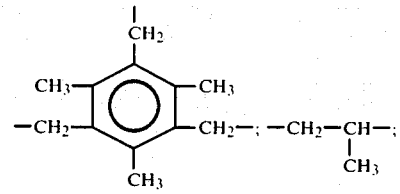

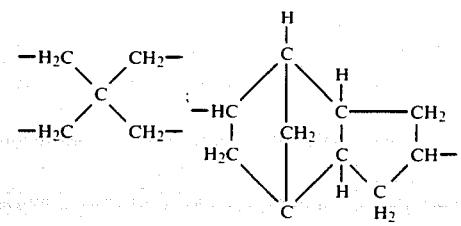

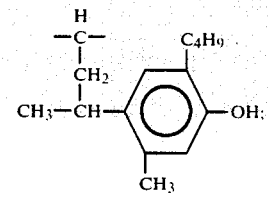

(2) Y groups where only atoms other than carbon link the aromatic rings, such as $$-O-, -S-, -\overset{O}{\underset{O}{\overset{\|}{S}}}-, -\overset{O}{\underset{O}{\overset{\|}{S}}}- \text{ and } -(S)_x-$$

where x is a number from one to ten;

(3) Y groups made up of more than a single atom including both carbon and other atoms linking the aromatic nuclei, such as:

—CH₂—O—CH₂—; —CH—CH₂—O—CH₂—CH—;
　　　　　　　　　　CH₃　　　　　　　CH₃

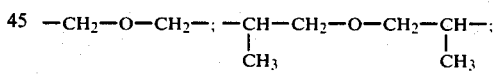

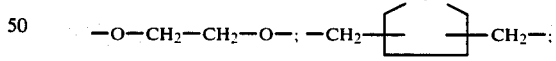

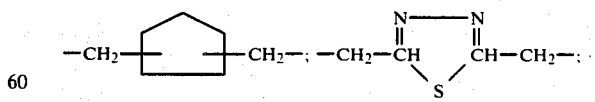

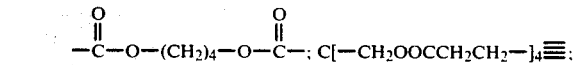

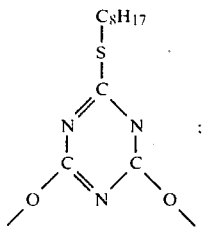

; —CH₂—S—; —CH₂—S—CH₂—; and

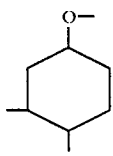

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenol, tetrahydro-α-naphthol, o-, m- and p-cresol, o-, m- and p-phenyl-phenol, o-, m- and p-xylenols, the carvenols, symmetrical xylenol, thymol, o-, m- and p-nonylphenol, o-, m- and p-dodecyl-phenol, and o-, m- and p-octyl-phenol, o-, and m-tert-butyl-p-hydroxy-anisole, p-n-decyloxy-phenol, p-n-decyloxy-cresol, nonyl-n-decyloxy-cresol, eugenol, isoeugenol, glyceryl monosalicylate, methyl-p-hydroxy-cinnamate, 4-benzyloxy-phenol, p-acetylaminophenol, p-stearyl-aminophenol, methyl-p-hydroxybenzoate, p-di-chlorobenzoyl-aminophenol, p-hydroxysalicyl anilide, -stearyl-(3,5-di-methyl-4-hydroxy-benzyl)thioglycolate, stearyl-β-(4-hydroxy-3,5-di-t-butylphenyl) propionate, distearyl-3,5-di-t-butyl-4-hydroxybenzylphosphonate, and distearyl (4-hydroxy-3-methyl-5-t-butyl) benzylmalonate.

Exemplary polyhydric phenols are orcinol, propyl gallate, catechol, resorcinol, 4-octyl-resorcinol, 4-dodecylresorcinol, 4-octadecyl-catechol, 4-isooctyl-phloroglucinol, pyrogallol, hexahydroxybenzene, 4-isohexylcatechol, 2,6-di-tertiary-butyl-resorcinol, 2,6-di-isopropyl-phloroglucinol.

Exemplary polyhydric polycyclic phenols are methylene bis-(2,6-di-tertiary-butyl-phenol), 2,2-bis-(4-hydroxy phenyl)-propane, methylene-bis-(p-cresol), 4,4'-benzylidene bis (2-tertiary-butyl-5-methyl-phenol), 4,4'-cyclo-hexylidene bis-(b 2-tertiary-butylphenol), 2,2'-methylene-bis-(4-methyl-6-(1'-methyl-cyclohexyl)-phenol), 2,6-bis-(2'-hydroxy-3'-tertiarybutyl-5'-methyl-benzyl)-4-methylphenol, 4,4'-bis-(2-tertiary-butyl-5-methyl-phenol), 2,2'-bis-(4-hydroxy-phenyl) butane, ethylene bis-(p-cresol), 4,4'-oxobis-phenol, 4,4'-oxobis-(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol; 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methylphenol), 2,2'-methylene-bis-(4-methyl-6-(1'-methyl-cyclohexyl)phenol), 4,4'-cyclohexylene bis-(2-tertiary-butyl-phenol), 2,6-bis-(2'-hydroxy-3'-t-butyl-5'-methyl-benzyl)-4-methylphenol, 4,4'-oxobis (naphthalene-1,5-diol), 1,3'-bis-(naphthalene-2,5-diol) propane, and 2,2'-butylene bis-(naphthalene-2,7-diol), (3-methyl-5-tert-butyl-4-hydroxy-phenyl)-4'-hydroxy-phenyl)propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenol), (3,5-di-tert-butyl-4-hydroxyphenyl)-(4'hydroxyphenyl)ethane, (2-hydroxyphenyl)-(3',5'-di-tert-butyl-4',4-hydroxyphenyl) ethane, 2,2'-methylene-bis-(4-octylphenol), 4,4'-propylene-bis-(2-tert-butyl-phenol), 2,2'-isobutylene-bis-(4-nonyl-phenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 2,2'-bis -(3-t-butyl-4-hydroxyphenyl)thiazolo-(5,4-d)thiazole, 2,2'-bis-(3-methyl-5-t-butyl-4-hydroxyphenyl)thiazolo-(5,4-d)-thiazole, 4,4'-bis-(4-hydroxyphenyl)pentanoic acid octadecyl ester, cyclopentylene-4,4'-bis-phenol, 2-ethylbutylene-4,4'-bisphenol, 4,4'-cyclooctylene-bis-(2-cyclohexylphenol), β,β-thiodiethanol-bis-(3-tert-butyl-4-hydroxyphenoxy acetate), 1,4-butanedio-bis-(3-tert-butyl-4-hydroxyphenoxy acetate), pentaerythritol tetra-(4-hydroxyphenol propionate), 2,4,4'-tri-hydroxy benzophenone, bis-(2-tert-butyl-3-hydroxy-5-methylphenyl)sulfide, bis-(2-tert-butyl-4-hydroxy-5-methylphenyl)sulfide, bis-(2-tert-butyl-4-hydroxy-5-methylphenyl)sulfoxide, bis-(3-ethyl-5-tert-butyl-4-hydroxybenzyl)sulfide, bis-(2-hydroxy-4-methyl-6-tert-butyl-phenyl)sulfide, 4,4'-bis-(4-hydroxyphenol)pentanoic acid octadecyl thiopropionate ester, 1,1,3-tris-(2'-methyl-4-hydroxy-5'-tert-butylphenyl)butane, 1,1,3-tris-(1-methyl-3-hydroxy-4-tert-butylphenyl)butane, 1,8-bis-(2-hydroxy-5-methyl-benzoyl-n-octane, 2,2'-ethylene-bis-[4'-(3-tert-butyl-4-hydroxyphenyl)-thiazole], 1-methyl-3-(3-methyl-5-tert-butyl-4-hydroxybenzyl)-naphthalene, 2,2'-(2-butene)-bis-(4-methoxy-6-tert-butylphenol)-bis-[3,3-bis-(4-hydroxy-3-t-butylphenyl)butyric acid]glycol ester, 4,4'-butylidene-bis-(6-t-butyl-m-cresol), 1,1,3-tris-(2-methyl-4-hydroxy-5-t-butylphenyl)butane, 1,3,5-tris-(3,5-di-t-butyl-4-hydroxybenzyl)-2,4,6-trimethylbenzene, tetrakis[methylene-3(3,5-di-t-butyl-4-hydroxyphenyl)propionate]methane, 1,3,5-tris-(3,5-di-t-butyl-4-hydroxybenzyl)isocyanurate, 1,3,5-tris-(3,5-di-t-butyl-4-hydroxyphenyl)propionyl-oxyethyl isocyanurate, 2-octylthio-4,6-di-(4-hydroxy-3,5-di-t-butyl)phenoxy-1,3,5-triazine, 4,4'-thiobis-(6-t-butyl-m-cresol) and pentaerythritol hydroxyphenyl propionate.

A particularly desirable class of polyhydric polycyclic phenols are the dicyclopentadiene polyphenols, which are of the type:

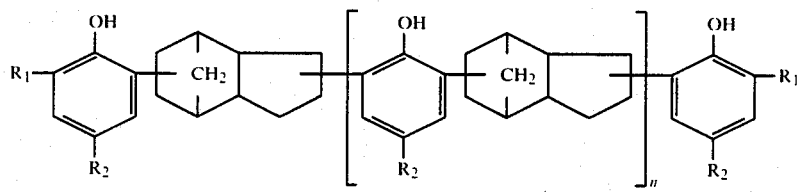

in which

R$_1$ and R$_2$ are lower alkyl, and can be the same or different, and n is the number of the groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopentadiene tri-(2-tert-butyl-4-methyl-phenol) of the formula:

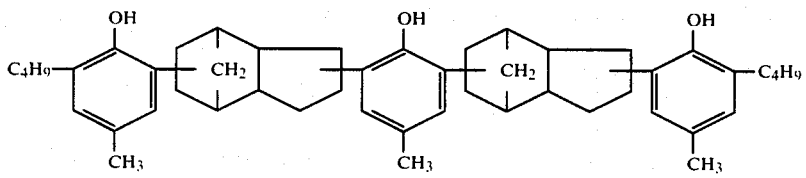

The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see e.g., U.S. Pat. No. 3,124,555, U.S. Pat. No. 3,242,135, and British Pat. No. 961,504.

When the stabilizer composition is used in conjunction with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkylsubstituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, iooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

The thiodipropionic acid ester has the following formula:

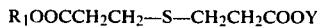

in which R$_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen; (b) a second R radical R$_2$, which can be the same as or different from the R$_1$ radical, (c) a polymeric chain of n thiodipropionic acid ester units:

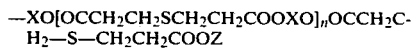

where Z is hydrogen, R$_2$ or M, n is the number of thiodipropionic acid ester units in the chain, and X is a bivalent hydrocarbon group of the type of R$_1$, that is, alkylene, alkenylene, cycloalkylene, mixed alkylene-arylene and mixed alkylene-cycloalkylene radicals; hydroxyalkylene and hydroxyalkyloxyalkylene radicals; and esters thereof with aliphatic carboxylic acids; the value of n can range upwards from 0, but there is no upper limit on n except as is governed by the ratio of carbon atoms to sulfur atoms as stated below; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

Accordingly, the various thiodipropionic acid ester species coming with the above-designated catagories within the general formula can be defined as follows:

$R_1OOCCH_2CH_2SCH_2CH_2COOH$     (a)

$R_1OOCCH_2CH_2SCH_2CH_2COOR_2$     (b)

$R_1O[OCCH_2CH_2SCH_2CH_2COOX\!-\!O]\!-\!_nOCCH_2CH_2SCH_2CH_2COOZ$     (c)

$R_1OOCCH_2CH_2SCH_2CH_2COOM$     (d)

In the above formulae $R_1$ and $R_2$, M, X and Z are the same as before and the value of $n_1$ can range upwards from 1, but there is no upper limit on $n_1$ except as is imposed by the ratio of carbon atoms, as stated below. In the polymer (c), as in the other forms of thiodipropionic acid esters, the total number of carbon atoms per sulfur atom is within the range from about ten to about sixty.

The R radical of these esters is important in furnishing compatibility with the polymer. The Y radical is desirably a different radical, $R_2$ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described above.

The aryl, alkyl, alkenyl, and cycloalkyl groups may, if desired, contain inert, nonreactive substituents, such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl-substituted alkylene radicals such as 1,2-propylene,

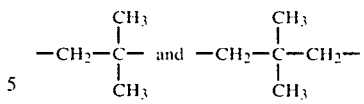

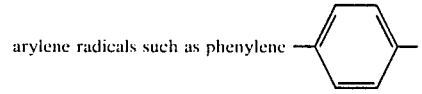

arylene radicals such as phenylene

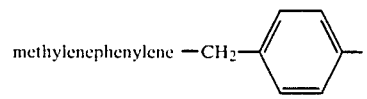

methylenephenylene $-CH_2-$

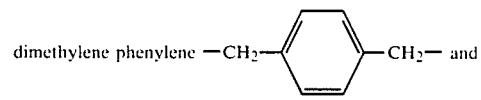

dimethylene phenylene $-CH_2-$ ... $-CH_2-$ and

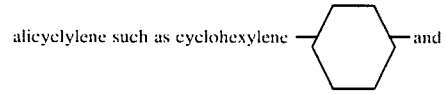

alicyclylene such as cyclohexylene ... and

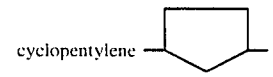

cyclopentylene

As exemplary of the thiodipropionic acid esters which can be used, there can be mentioned the following: monolauryl thiodipropionic acid; dilauryl thiodipropionate, butyl stearyl thiodipropionate, 2-ethylhexyl lauryl thiodipropionate, di-2-ethylhexyl-thiodipropionate, diisodecyl thiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soyabean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl)thiodipropionic acid.

These esters are for the most part known compounds, but where they are not available, they are readily prepared by esterification of thiodipropionic acid and the corresponding alcohol.

Also useful are:

(1) Thioalkanoic acid amides of Tokuno et al Japanese Pat. No. 16,286/68 having the formula:

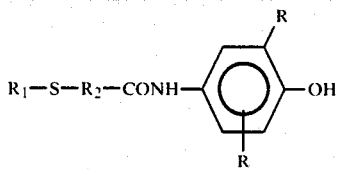

R is alkyl of one to eight carbon atoms, R₁ is alkyl of six to twenty-four carbon atoms, and R₂ is alkylene of one to six carbon atoms.

(2) Thioalkanoic acid amides of 1,3,5-triazines of Ozeki et al Japanese Pat. No. 20,366/68 having the formula:

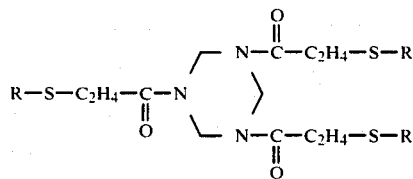

R is alkyl of eight to eighteen carbon atoms.

(3) Bis-thioalkanoic acid amides of Yamamoto et al Japanese Pat. No. 23,765/68 having the formula:

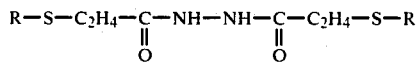

R is alkyl of more than six carbon atoms, aryl or aralkyl.

(4) Bis-thioalkylanoic acid amides of Ozeki et al Japanese Pat. No. 26,184/69 having the formula:

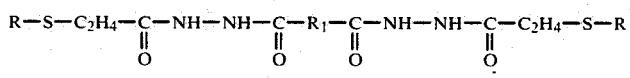

R is alkyl of twelve to eighteen carbon atoms, and R₁ is alkylene of one to ten carbon atoms, cycloalkylene, or arylene.

(5) Bis-alkylene thioalkanoic acid amides of Ozeki Japanese Pat. No. 31,464/69 having the formula:

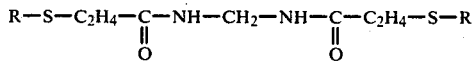

R is alkyl of more than six carbon atoms, aryl, or aralkyl.

(6) Thioalkanoic acid amide derivatives of Minagawa et al, published Japanese application No. 106,484/74 having the formula:

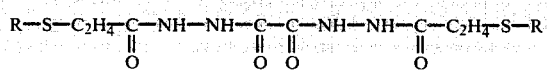

R is hydrocarbyl of one to twenty carbon atoms.

(7) Alkylene bis-thioalkanoic acid amides of U.S. Pat. No. 4,279,805 to Ohzeki et al, patented July 21, 1981, having the general formula:

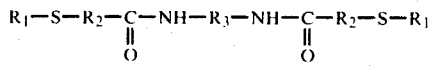

wherein:
R₁ is alkyl having from one to about fifty carbon atoms;
R₂ is alkylene having from one to about three carbon atoms; and
R₃ is alkylene having from about two to about twelve carbon atoms.

β-Alkylthiopropionic acid esters having the general formula:

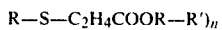

wherein:
R is alkyl of four to twenty carbon atoms;
n is a number from 1 to 6; and
R' is the residue of an alcohol having from one to six hydroxyl groups.

Pentaerythritol tetra dodecyl thio propionate is an example of this group.

In addition, the usual light stabilizers can be employed, such as 2,2,6,6-tetramethyl piperidyl compounds, hydroxybenzophenones such as 2-hydroxy-4-methoxybenzophenone, 2-hydroxy-4-n-octoxy benzophenone, 2,4-dihydroxybenzophenone, benzotriazoles, such as 2(2-hydroxy-5-methylphenyl)benzotriazoles, 2(2-hydroxy-3-t-butyl-5-methylphenyl)-5-chlorobenzotriazole, 2(2-hydroxy-3-5-di-t-butylphenyl)5-chlorobenzotriazole, 2(2-hydroxy-3,5-di-t-amylphenyl)benzotriazole, benzoates such as phenylsalicylate, 2,4-di-t-butylphenyl-3,5-di-t-butyl-4-hydroxy phenylbenzoate, nickel compounds such as nickel-2,2-'-thiobis(4-t-octyl phenolate), nickel-monoethyl(3,5-di-t-butyl-4-hydroxybenzyl)phosphonate, substituted acrylonitriles such as methyl-α-cyano-β-methyl-β-(p-methoxy phenyl)acrylate and oxalic anilides such as N-2-ethyl phenyl-N'-2-ethoxy-5-t-butyl phenyl oxalic diamide, N-2-ethyl phenyl-N'-2-ethoxy phenyl oxalic diamide.

A sufficient amount of the stabilizer or combination is used to improve the resistance of the synthetic polymer to deterioration in physical properties when exposed to heat and light, including, for example, discoloration, reduction in melt viscosity and embrittlement. Very small amount are usually adequate. Amounts within the range from about 0.001 to about 10% total stabilizers including the heat and light stabilizer of the invention by weight of the polymer are satisfactory. Preferably, from 0.01 to 5% is employed for optimum stabilization.

When all components are solids, the stabilizer systems of the invention are readily rendered in solid particulate form, comprising a blend of:
(a) alkylidene bisphenol phosphite and phosphate in an amount of from about 10 to about 35 parts by weight; and optionally:
(b) a phenolic antioxidant in an amount from about 10 to about 35 parts by weight; and/or
(c) other heat or light stabilizers in an amount of from about 10 to about 35 parts by weight.

The alkylidene bisphenol phosphite and phosphate of the invention can be employed in combination with phenolic antioxidant and/or other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organotin compounds; and epoxy compounds.

With polyolefin resins there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylonitrile-butadiene-styrene terpolymers, other antioxidants and polyvalent metal salts of the higher fatty acids can be used.

In addition, other conventional additives for synthetic polymers, such as plasticizers, lubricants, emulsifiers, antistatic agents, flame-proofing agents, pigments and fillers, can be employed.

The stabilizer or combination is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following Examples illustrate preferred stabilizer systems and resin compositions of the invention:

EXAMPLES 1 TO 6

Polypropylene compositions were prepared using stabilizers of this invention and two of the prior art, and having the following formulation:

| Ingredient | Parts by Weight |
|---|---|
| Unstabilized polypropylene | 100 |
| Calcium stearate | 0.2 |
| Pentaerythritol tetrakis(3,5-di-t-butyl-4-hydroxyphenylpropionate) | 0.1 |
| Stabilizer as shown in Table I | 0.2 |

The compositions were thoroughly blended in a Brabender Plastograph, and then compression-molded to form sheets 0.3 mm thick. Pieces 2.5 cm$^2$ were cut off from the sheets and exposed to a high voltage mercury lamp. The hours to failure were noted.

The compositions were each extruded at 300° C. for five times, and the melt flow index (MFI) (at 230° C., load: 2160 g) was measured. The ratio of MFI (MFI after extruded five times (MFI-5)/MFI after extruded one time (MFI-1) was also determined. The results are shown in Table I.

TABLE I

| Example No. | Stabilizer | Hours to Failure | MFI-5/ MFI-1 |
|---|---|---|---|
| Control 1 | None | 120 | 4.1 |
| Control 2 | 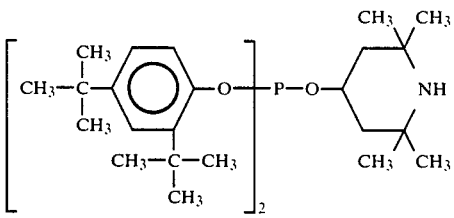 | 250 | 3.5 |
| Control 3 | 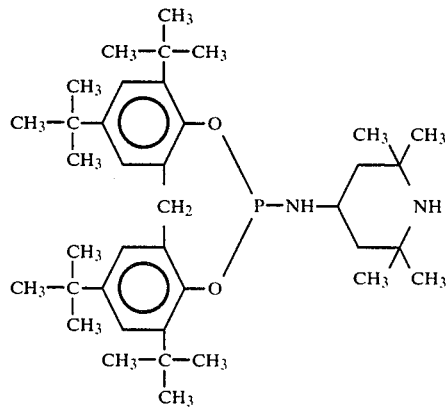 | 220 | 3.2 |

TABLE I-continued
| Example No. | Stabilizer | Hours to Failure | MFI-5/ MFI-1 |
|---|---|---|---|
| Example 1 | 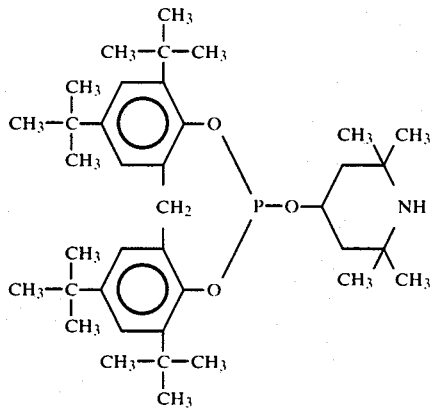 | 370 | 1.9 |
| Example 2 | 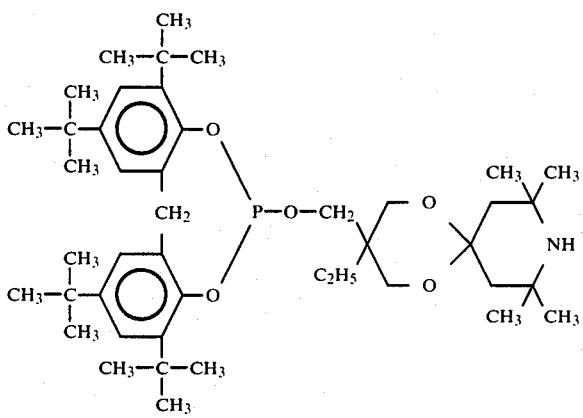 | 350 | 1.8 |
| Example 3 | 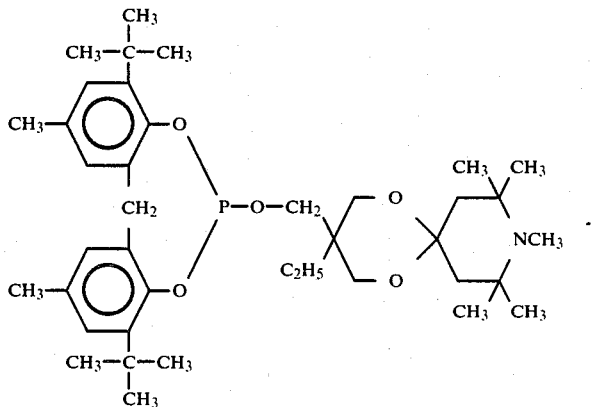 | 350 | 1.8 |

TABLE I-continued

| Example No. | Stabilizer | Hours to Failure | MFI-5/MFI-1 |
|---|---|---|---|
| Example 4 | (structure shown) | 330 | 2.1 |
| Example 5 | (structure shown) | 300 | 2.4 |
| Example 6 | (structure shown) | 300 | 2.0 |

The superiority of the bisphenol phosphites and phosphates of the invention to the prior art compounds is apparent from the data.

EXAMPLES 7 TO 12

High density polyethylene compositions were prepared using stabilizers of the invention and two of the prior art, and having the following formulation:

| Ingredient | Parts by Weight |
|---|---|
| High-density polyethylene | 100 |
| Calcium stearate | 1.0 |
| Stearyl-3,5-di-t-butyl-4-hydroxyphenylpropionate | 0.1 |
| Stabilizer as shown in Table II | 0.2 |

The stabilizer was blended with the polymer on a two-roll mill and sheets 0.5 mm thick were prepared by compression-molding of the blend. Pieces 2.5 cm square were cut off from the sheets, and exposed in a Weather-O-Meter to ultraviolet light, and heated at 150° C. in a Geer oven on aluminum foil. The time in hours when degradation set in, as determined by a significant discoloration and/or embrittlement, was noted as hours to failure. The results are shown in Table II.

TABLE II

| Example No. | Stabilizer | Hours to Failure | |
|---|---|---|---|
| | | Geer oven | Weather-O-Meter |
| Control 1 | [structure: bis(2,4-di-tert-butylphenyl) phosphite with 2,2,6,6-tetramethylpiperidinyl-oxy group] | 680 | 460 |
| Control 2 | [structure: bis(3,5-di-tert-butyl-2-hydroxybenzyl) phosphoramidite with 2,2,6,6-tetramethylpiperidinyl-NH group] | 620 | 510 |
| Example 7 | [structure: bis(3,5-di-tert-butyl-2-hydroxybenzyl) phosphite with 1,2,2,6,6-pentamethylpiperidinyl-oxy group] | 930 | 680 |
| Example 8 | [structure: bis(3,5-di-tert-butyl-2-hydroxybenzyl) phosphite with spiro-dioxane 2,2,6,6-tetramethylpiperidine group] | 900 | 660 |

TABLE II-continued
| Example No. | Stabilizer | Hours to Failure Geer oven | Weather-O-Meter |
|---|---|---|---|
| Example 9 | 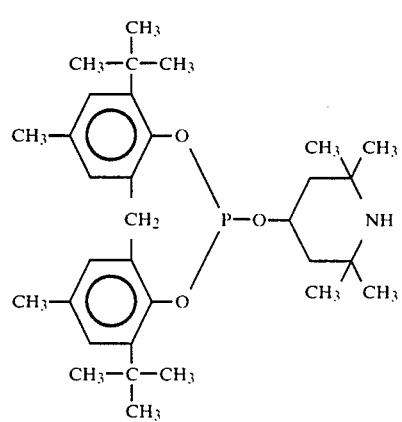 | 930 | 700 |
| Example 10 | 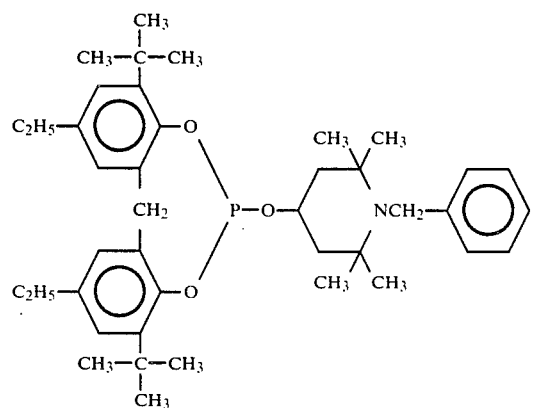 | 860 | 650 |
| Example 11 | 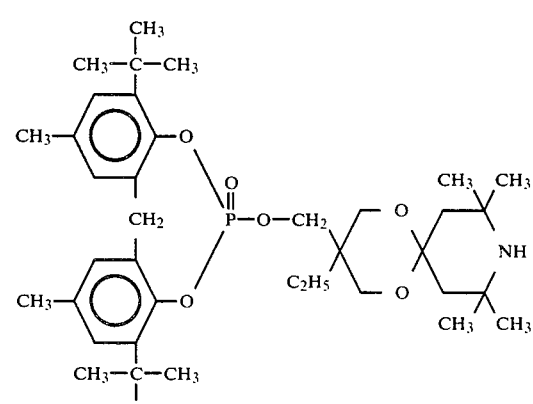 | 840 | 600 |

TABLE II-continued

| Example No. | Stabilizer | Hours to Failure | |
|---|---|---|---|
| | | Geer oven | Weather-O-Meter |
| Example 12 | [bisphenol phosphite structure with two substituted bisphenol groups connected via P—O—CH₂—C(C₂H₅)(CH₂O—)₂ spiro unit and NC₂H₄O—P linkage] | 800 | 650 |

The superiority of the bisphenol phosphites and phosphates of the invention to the prior art compounds is apparent from the data.

EXAMPLES 13 TO 18

A group of polyvinyl chloride resin compositions was prepared having the following formulation:

| Ingredient | Parts by Weight |
|---|---|
| Polyvinyl chloride | 100 |
| Di-2-ethylhexylphthalate | 45 |
| Tricresylphosphate | 5 |
| Bisphenol A.diglycidylether | 3 |
| Zinc stearate | 0.6 |
| Barium stearate | 0.3 |
| Barium nonylphenolate | 0.3 |
| Sorbitan monopalmitate | 2.0 |
| Methylenebis(stearamide) | 0.3 |
| Stabilizer as shown in Table III | 0.3 |

This formulation was blended and sheeted off on a two-roll mill to form sheets 0.1 mm thick.

The sheets were heated in air in a Geer oven at 190° C. to evaluate heat stability, and the time in minutes noted for the sheet to develop a noticeable discoloration and/or embrittlement.

The light stability of these sheets was determined by placing the sheets in a Weather-O-Meter, and exposing them to ultraviolet light. The time in hous was then noted for the sheets to develop a noticeable discoloration and/or embrittlement. The results are shown in Table III.

TABLE III

| Example No. | Stabilizer | Heat Stability (minutes) | Light Stability (hours) |
|---|---|---|---|
| Control 1 | Octyl diphenyl phosphite | 100 | 1200 |
| Control 2 | [bis(di-tert-butylphenyl) phosphite with tetramethylpiperidinyl NH group] | 105 | 2200 |

TABLE III-continued

| Example No. | Stabilizer | Heat Stability (minutes) | Light Stability (hours) |
|---|---|---|---|
| Control 3 | (structure) | 110 | 2500 |
| Example 13 | (structure) | 130 | 4400 |
| Example 14 | (structure) | 120 | 3600 |

TABLE III-continued
| Example No. | Stabilizer | Heat Stability (minutes) | Light Stability (hours) |
|---|---|---|---|
| Example 15 | 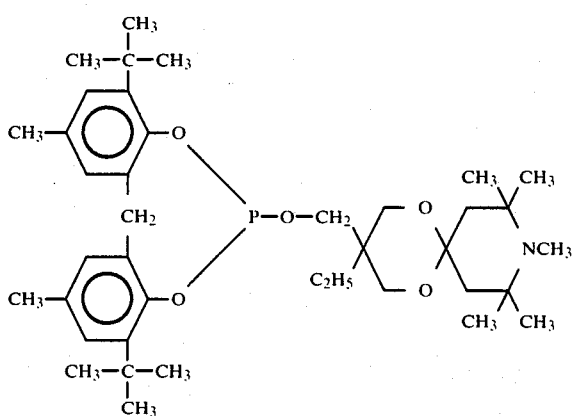 | 135 | 4200 |
| Example 16 | 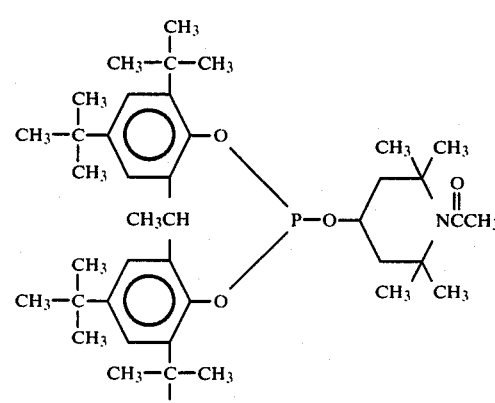 | 125 | 3500 |
| Example 17 | 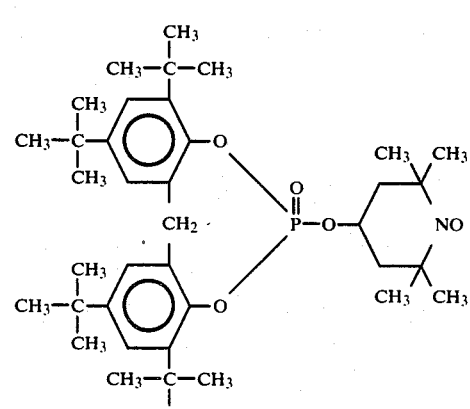 | 130 | 4200 |

TABLE III-continued

| Example No. | Stabilizer | Heat Stability (minutes) | Light Stability (hours) |
|---|---|---|---|
| Example 18 | 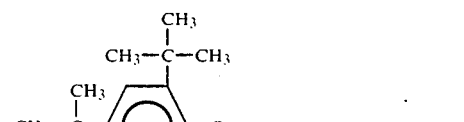 | 120 | 3500 |

The superiority of the bisphenol phosphites and phosphates of the invention to the prior art compounds is apparent from the data.

EXAMPLES 19 TO 24

Acrylonitrile-butadiene-styrene terpolymer resin compositions were prepared using stabilizers of the invention and two of the prior art, and having the following formulation:

| Ingredient | Parts by Weight |
|---|---|
| Acrylonitrile-butadiene-styrene terpolymer | 100 |
| 4,4'-Butylidene-bis(2-t-butyl-m-cresol) | 0.1 |
| Stabilizer as shown in Table IV | 0.3 |

The stabilizer was blended with the resin on a two-roll mill, and sheets 3 mm thick were prepared by compression molding of the resulting blend.

Pieces 2.5 cm square were cut off from the sheets, and exposed to ultraviolet light in a Weather-O-Meter for 800 hours. Tensile strength before and after the exposure was determined, and the results reported as the percent of tensile strength retained, at the end of this time, in Table IV. Heat stability was evaluated by heating the specimen sheets at 210° C. for ten minutes. The color of the specimens was noted and graded on a scale from 1 to 10, in which 1 shows white and 10 shows brown. The results are shown in Table IV.

TABLE IV

| Example No. | Stabilizer | % Retention of Tensile Strength | Color of Sheets |
|---|---|---|---|
| Control 1 |  | 50 | 5 |

TABLE IV-continued
| Example No. | Stabilizer | % Retention of Tensile Strength | Color of Sheets |
|---|---|---|---|
| Control 2 | 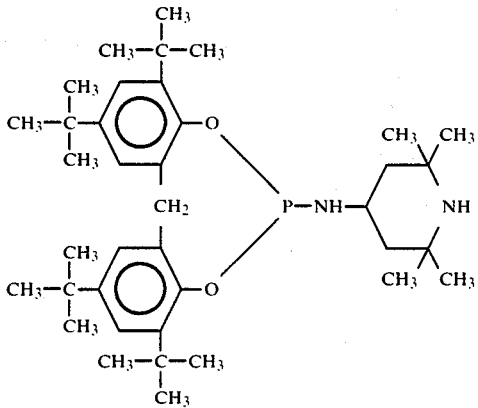 | 48 | 6 |
| Example 19 | 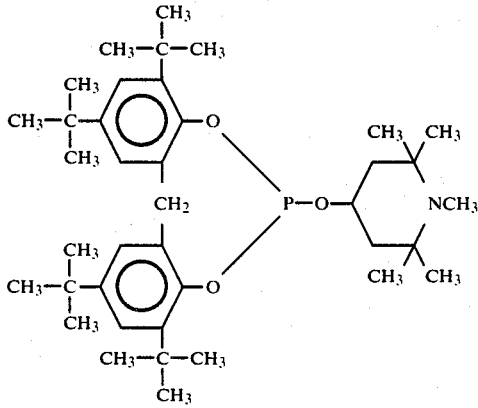 | 74 | 2 |
| Example 20 | 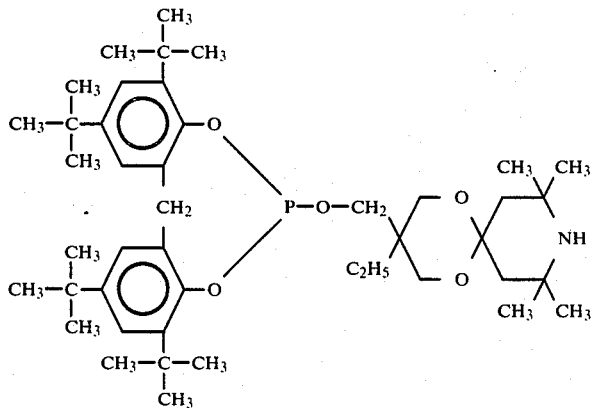 | 75 | 2 |

TABLE IV-continued

| Example No. | Stabilizer | % Retention of Tensile Strength | Color of Sheets |
|---|---|---|---|
| Example 21 | (structure) | 75 | 2 |
| Example 22 | (structure) | 72 | 3 |
| Example 23 | (structure) | 73 | 4 |

TABLE IV-continued

| Example No. | Stabilizer | % Retention of Tensile Strength | Color of Sheets |
|---|---|---|---|
| Example 24 | (bisphenol phosphite structure with two di-tert-butyl substituted bisphenol groups linked through P—O to a 2,2,6,6-tetramethylpiperidinyl-oxy group, dimeric via NC₂H₄O—P) | 70 | 2 |

The superiority of the bisphenol phosphites and phosphates of the invention to the prior art compounds is apparent from the data.

EXAMPLES 25 TO 30

Polyurethane resin compositions were prepared using stabilizers of the invention and two of the prior art, and having the following formulation:

| Ingredient | Parts by Weight |
|---|---|
| Polyurethane resin (Asahi Denka U-100)[1] | 100 |
| Barium stearate | 0.7 |
| Zinc stearate | 0.3 |
| Stabilizer as shown in Table V | 0.3 |

[1] A polyurethane-isocyanate made from toluene diisocyanate and alkylene polyol.

The stabilizer was blended with the finely powdered polyurethane resin on a two-roll mill for five minutes at 70° C., and the sheet was then compression-molded at 120° C. for five minutes to form sheets 0.5 mm thick. Pieces 2.5 cm square were cut off from the sheets, and exposed to ultraviolet light in a Fade-O-Meter for fifty hours. Elongation before and after exposure was determined, and the percent elongation retained after the exposure is given in Table V.

TABLE V

| Example No. | Stabilizer | % Retention of Elongation |
|---|---|---|
| Control 1 | (bis[di-tert-butyl bisphenol]—O—P—O—2,2,6,6-tetramethylpiperidinyl-NH), bracketed ×2 | 52 |
| Control 2 | (bisphenol phosphite with P—NH—2,2,6,6-tetramethylpiperidinyl-NH group) | 48 |

TABLE V-continued
| Example No. | Stabilizer | % Retention of Elongation |
|---|---|---|
| Example 25 | 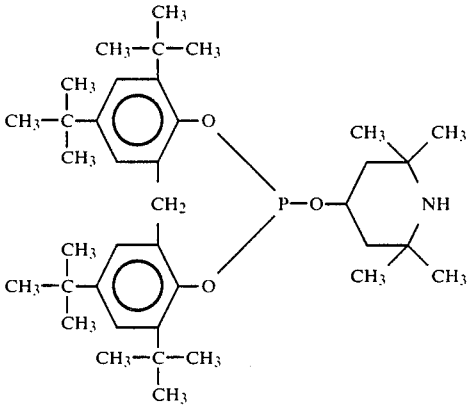 | 66 |
| Example 26 | 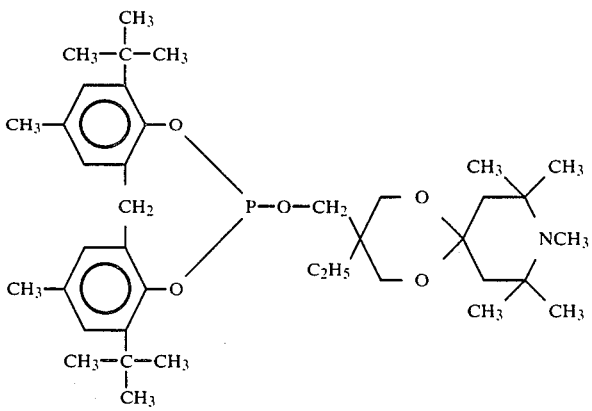 | 65 |
| Example 27 | 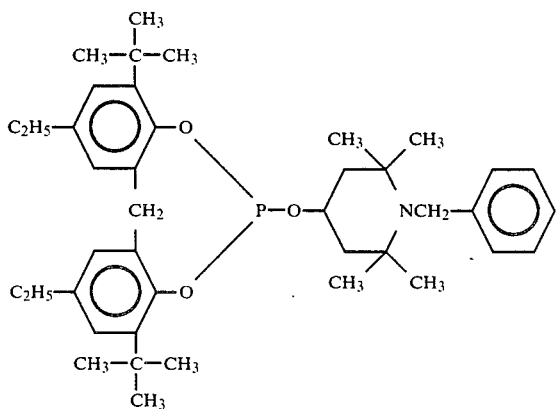 | 62 |

TABLE V-continued

| Example No. | Stabilizer | % Retention of Elongation |
|---|---|---|
| Example 28 | 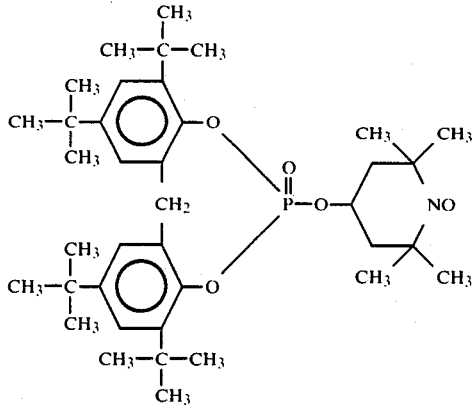 | 62 |
| Example 29 | 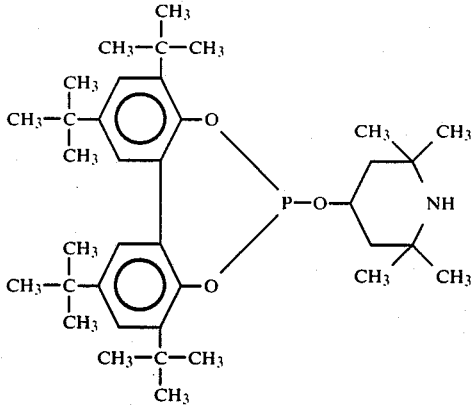 | 60 |
| Example 30 | 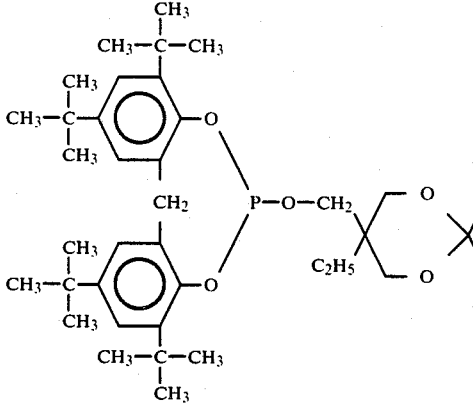 | 63 |

The superiority of the bisphenol phosphites and phosphates of the invention to the prior art compounds is apparent from the data.

EXAMPLES 31 TO 36

The stabilizers of this invention are effective as light stabilizers for coatings.

The effect of the stabilizers in a two-coat metallic effect finish comprising metallic effect priming lacquer and unpigmented finishing lacquer was determined.

(a) Metallic effect priming lacquer

An acrylic resin solution was prepared by heating and stirring a mixture of methyl methacrylate 100 g, n-butylacrylate 66 g, 2-hydroxyethyl methacrylate 30 g, methacrylic acid 4 g, xylene 80 g and n-butanol 20 g at 110° C. while adding a solution of azobisisobutyronitrile 2 g, dodecylmercaptan 0.5 g, xylene 80 g and n-butanol 20 g dropwise over three hours. The solution was then stirred an additional two hours at 110° C.

The above acrylic resin solution 12 parts, butoxylated methylolmelamine (Mitsui-Toatsu Co., Yuban 20SE60; solids content 60%) 2.5 parts, cellulose acetobutyrate (20% butyl acetate solution) 50 parts, aluminum pigment (Toyo Aluminium Co., Alpaste 1123N) 5.5 parts, xylene 10 parts, butyl acetate 20 parts and copper phthalocyanine blue 0.2 part were blended.

(b) Unpigmented finishing lacquer

The above acrylic resin solution 48 parts, butoxylated methylolmelamine 10 parts, xylene 10 parts, butoxyethylacetate 4 parts and stabilizer as shown in Table VI 0.15 part were blended.

Pieces of steel sheeting, which were coated with a primer, were first coated with the priming lacquer and subsequently with the finishing lacquer. The printing lacquer was sprayed on to a thickness of about 20 microns, and aired for 10 minutes. Then the clear lacquer was sprayed on to a thickness of about 30 microns. After being aired 15 minutes, the samples were stoved for 30 minutes at 140° C.

The coated sheets were exposed to ultraviolet light in a Weather-O-Meter. The time in hours when degradation set in, as determined by cracking of a surface of the sheet, was noted as hours to failure, and the results are shown in Table VI.

TABLE VI

| Example No. | Stabilizer | Hours to Failure |
|---|---|---|
| Control 1 | [structure] | 2600 |
| Control 2 | [structure] | 2800 |
| Example 31 | [structure] | 4400 |

TABLE VI-continued
| Example No. | Stabilizer | Hours to Failure |
|---|---|---|
| Example 32 | 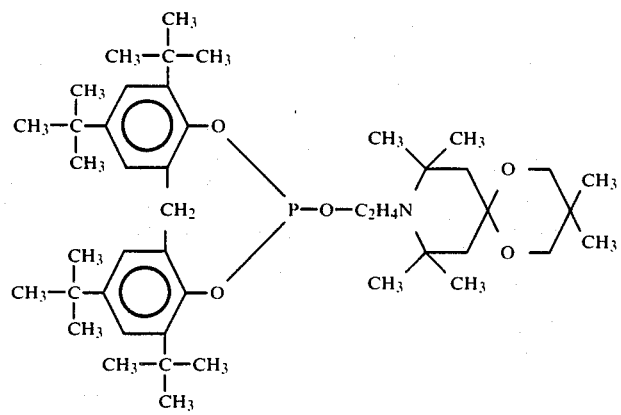 | 3700 |
| Example 33 | 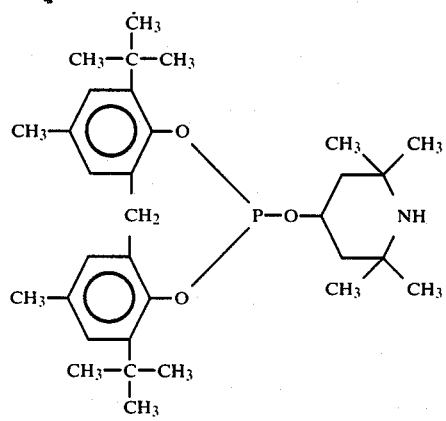 | 4100 |
| Example 34 | 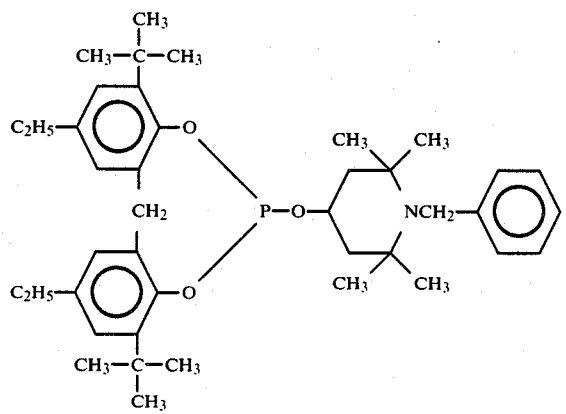 | 4000 |

TABLE VI-continued

| Example No. | Stabilizer | Hours to Failure |
|---|---|---|
| Example 35 | 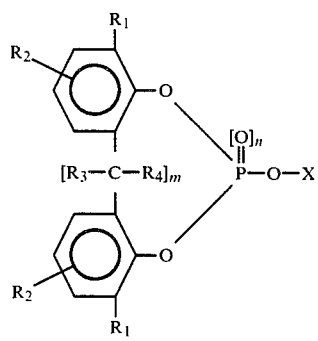 | 3800 |
| Example 36 | | 3800 |

The superiority of the bisphenol phosphites and phosphates of the invention to the prior art compounds is apparent from the data.

Having regard to the foregoing disclosure the following is claimed as the inventive and patentable embodiments thereof:

1. Alkylidene bisphenol phosphites and phosphates having 2,2,6,6-tetramethyl piperidinyl groups having the formula:

I wherein:

$R_1$ is alkyl having from one to about twelve carbon atoms;

$R_2$, $R_3$ and $R_4$ are each selected from the group consisting of hydrogen and alkyl having from one to about twelve carbon atoms;

m is 0 or 1;

n is 0 or 1;

X is selected from the group consisting of

wherein:

$R_5$ is selected from the group consisting of hydrogen, oxyl O, alkyl having from one to about twelve carbon atoms; aryl alkyl having from seven to about eighteen carbon atoms; 2,3-epoxypropyl, acyl having from one to about eight carbon atoms and

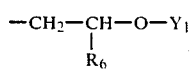

in which $R_6$ is selected from the group consisting of hydrogen, alkyl having from one to about twelve carbon atoms and phenyl, and $Y_1$ is selected from the group consisting of hydrogen; acyl having from one to about twelve carbon atoms; and $$\begin{array}{c} R_1 \\ \phantom{x} \\ [O]_n \\ \phantom{x} \\ -P \phantom{xx} [R_3-C-R_4]_m \\ \phantom{x} \\ O \\ \phantom{x} \\ R_2 \\ R_1 \end{array}$$

$Z_1$ is selected from the group consisting of $$-CH\begin{array}{c}-CH_2\\ \\ R_7\end{array} \text{ and } \begin{array}{c}-CH_2\\ \diagdown \\ C \\ \diagup \\ R_7\end{array}\begin{array}{c}CH_2-O\\ \diagdown \\ \diagup \\ CH_2-O\end{array}C\diagdown$$

wherein $R_7$ is alkyl having from one to about twelve carbon atoms;
and $$-CH-CH_2-N\begin{array}{c}CH_3\diagup CH_3\\ \diagup C\diagdown \\ \phantom{xx} Z_2 \\ \diagdown C\diagup \\ CH_3\diagup CH_3\end{array} \qquad (2)$$

$\phantom{-}R_6$ wherein:
$R_6$ is selected from the group consisting of hydrogen, alkyl having from one to about twelve carbon atoms and phenyl; and
$Z_2$ is selected from the group consisting of $$\diagdown C=O; \quad \diagdown CH-O-Y_2; \quad \begin{array}{c}\diagdown \diagup O\diagdown \\ C \phantom{xx} R_6 \\ \diagup \diagdown O \diagup\end{array} \text{ and}$$

$$\begin{array}{c}\diagdown \diagup OCH_2\diagdown \diagup CH_2-O-Y_2\\ C \phantom{xxxx} C \\ \diagup \diagdown OCH_2 \diagup \diagdown R_7\end{array}$$

in which $R_7$ is alkyl having from one to about twelve carbon atoms; $R_8$ is alkylene having from one to about eight carbon atoms and $Y_2$ is selected from the group consisting of hydrogen and acyl having from one to about eight carbon atoms.

2. Alkylidene bisphenol phosphites or phosphates according to claim 1 in which $R_1$ and $R_2$ are iso, secondary or tertiary alkyl having from three to about ten carbon atoms.

3. Alkylidene bisphenol phosphites or phosphates according to claim 1 in which $R_2$ is in a para position to the phenolic hydroxyl group.

4. Alkylidene bisphenol phosphites or phosphates according to claim 1 in which n is 0.

5. Alkylidene bisphenol phosphites or phosphates according to claim 1 in which n is 1.

6. Alkylidene bisphenol phosphites or phosphates according to claim 1 in which n is 0 and m is 0.

7. Alkylidene bisphenol phosphites or phosphates according to claim 1 in which n is 0 and m is 1.

8. Alkylidene bisphenol phosphites or phosphates according to claim 1 in which n is 1 and m is 0.

9. Alkylidene bisphenol phosphites or phosphates according to claim 1 in which n is 1 and m is 1.

10. Alkylidene bisphenol phosphites or phosphates according to claim 1 in which X is $$-Z_1\begin{array}{c}CH_3\diagup CH_3\\ \diagup C\diagdown \\ \phantom{xx} N-R_5 \\ \diagdown C\diagup \\ CH_3\diagup CH_3\end{array}$$

11. Alkylidene bisphenol phosphites or phosphates according to claim 10 in which $Z_1$ is $$-CH\diagdown$$

12. Alkylidene bisphenol phosphites or phosphates according to claim 10 in which $Z_1$ is $$\begin{array}{c}-CH_2\\ \diagdown \\ C \\ \diagup \\ R_7\end{array}\begin{array}{c}CH_2-O\\ \diagdown \\ \diagup \\ CH_2-O\end{array}C\diagdown$$

13. Alkylidene bisphenol phosphites or phosphates according to claim 1 in which X is $$-CH-CH_2-N\begin{array}{c}CH_3\diagup CH_3\\ \diagup C\diagdown \\ \phantom{xx} Z_2 \\ \diagdown C\diagup \\ CH_3\diagup CH_3\end{array}$$

$\phantom{-}R_6$

14. Alkylidene bisphenol phosphites or phosphates according to claim 13 in which $Z_2$ is $>C=O$.

15. Alkylidene bisphenol phosphites or phosphates according to claim 13 in which $Z_2$ is $>CH-O-Y_2$.

16. Alkylidene bisphenol phosphites or phosphates according to claim 13 in which $Z_2$ is $$\begin{array}{c}\diagdown \diagup O\diagdown \\ C \phantom{xx} R_6 \\ \diagup \diagdown O \diagup\end{array}$$

17. Alkylidene bisphenol phosphites or phosphates according to claim 13 in which $Z_2$ is $$\begin{array}{c}\diagdown \diagup OCH_2\diagdown \diagup CH_2-O-Y_2\\ C \phantom{xxxx} C \\ \diagup \diagdown OCH_2 \diagup \diagdown R_7\end{array}$$

18. Alkylidene bisphenol phosphites or phosphates according to claim 1 having the formula:

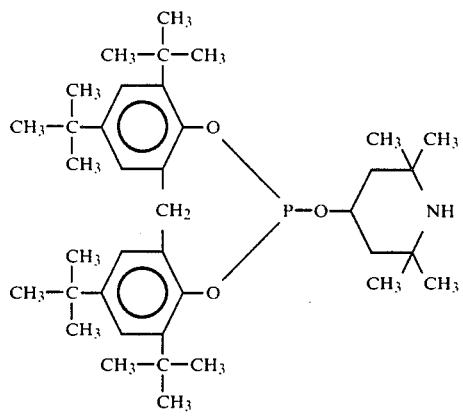

19. Alkylidene bisphenol phosphites or phosphates according to claim 1 having the formula:

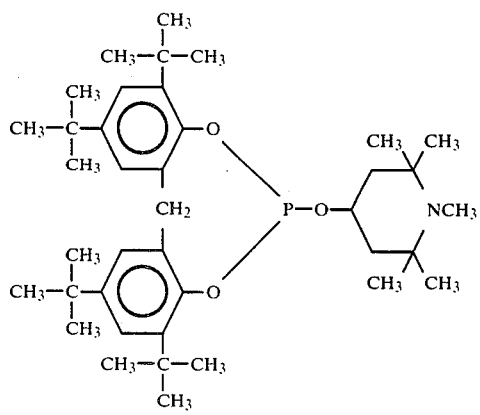

20. Alkylidene bisphenol phosphites or phosphates according to claim 1 having the formula:

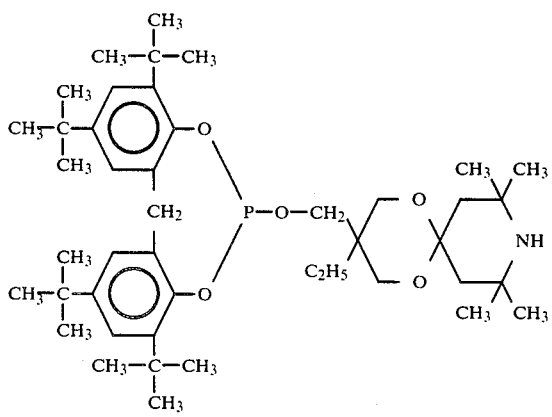

21. Alkylidene bisphenol phosphites or phosphates according to claim 1 having the formula:

22. Alkylidene bisphenol phosphites or phosphates according to claim 1 having the formula:

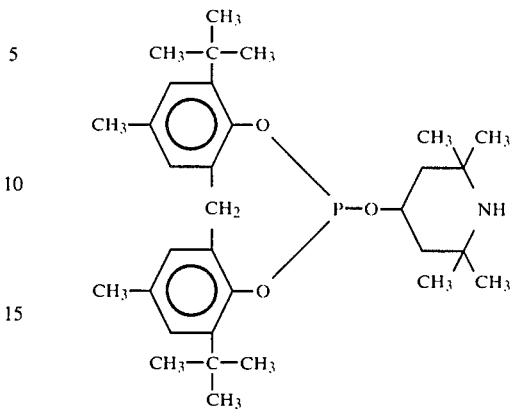

23. Alkylidene bisphenol phosphites or phosphates according to claim 1 having the formula:

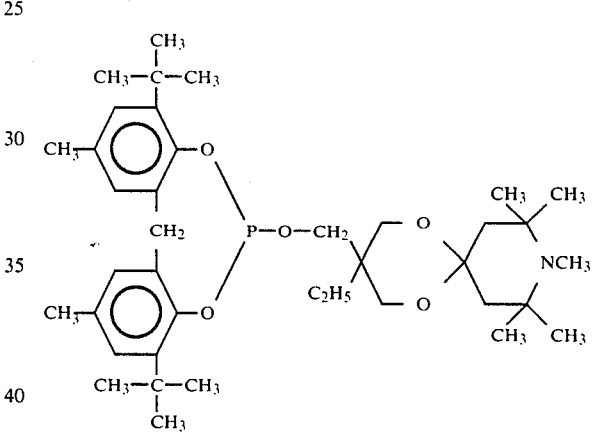

24. Alkylidene bisphenol phosphites or phosphates according to claim 1 having the formula:

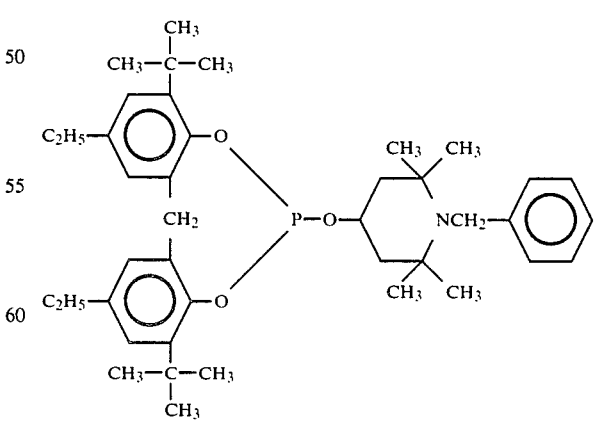

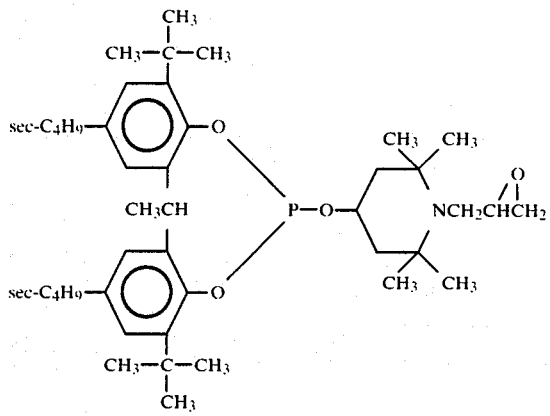

25. Alkylidene bisphenol phosphites or phosphates according to claim 1 having the formula:

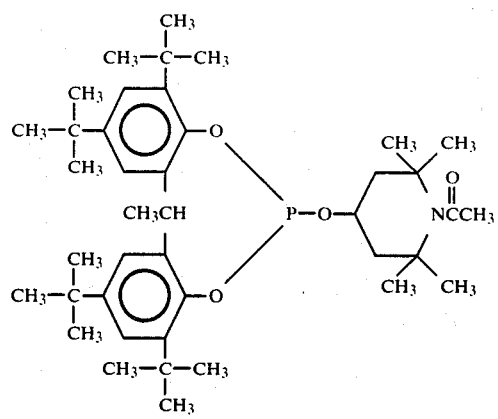

26. A polyvinyl chloride resin composition having improved resistance to deterioration to light comprising a polyvinyl chloride resin formed at least in part of the recurring group $$-CH-C-\underset{\underset{X}{|}}{\overset{\overset{X}{|}}{\underset{}{}}}-$$
$$\phantom{-CH-}\underset{Cl}{|}$$

and having a chlorine content in excess of 40%, where X is either hydrogen or chlorine; and an alkylidene bisphenol phosphite or phosphate in accordance with claim 1.

27. A polyvinyl chloride resin composition in accordance with claim 26, in which the polyvinyl chloride resin is polyvinyl chloride homopolymer.

28. A polyvinyl chloride resin composition in accordance with claim 26, in which the polyvinyl chloride resin is a copolymer of vinyl chloride and vinyl acetate.

29. An olefin polymer composition having improved resistance to deterioration when exposed to light comprising an olefin polymer selected from the group consisting of alpha-olefins having from two to six carbon atoms and polystyrene, and an alkylidene bisphenol phosphite or phosphate in accordance with claim 1.

30. An olefin polymer composition in accordance with claim 29 wherein the polyolefin is polypropylene.

31. An olefin polymer composition in accordance with claim 29 wherein the polyolefin is polyethylene.

32. An acrylonitrile-butadiene-styrene terpolymer having improved resistance to deterioration when exposed to light comprising acrylonitrile-butadiene-styrene terpolymer and an alkylidene bisphenol phosphite or phosphate in accordance with claim 1.

33. A polyurethane resin composition having improved resistance to deterioration when exposed to light comprising a polyurethane resin and an alkylidene bisphenol phosphite or phosphate in accordance with claim 1.

34. A light and heat stabilizer composition for improving the resistance to deterioration of synthetic polymers comprising an alkylidene bisphenol phosphite or phosphate in accordance with claim 1; and a synthetic polymer heat stabilizer selected from the group consisting of phenolic antioxidants, polyvalent metal salts of organic acids, organic phosphites, thioethers and thiodipropionic acid esters.

35. A light and heat stabilizer composition according to claim 34 in which the phenolic antioxidant has the formula:

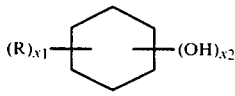

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl $$(R'\underset{\underset{O}{\|}}{C}-).$$

where $R'$ is aryl, alkyl or cycloalkyl;

$x_1$ and $x_2$ are integers from one to four, and the sum of $x_1$ and $x_2$ does not exceed six.

36. A light and heat stabilizer composition according to claim 34 in which the phenolic antioxidant has the formula:

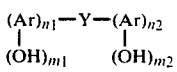

wherein

Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms;

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar;

$m_1$ and $m_2$ are numbers from one to five, and $n_1$ and $n_2$ are numbers of one or greater, and preferably from one to four.

* * * * *